US008951975B2

(12) United States Patent
Nakamura et al.

(10) Patent No.: US 8,951,975 B2
(45) Date of Patent: Feb. 10, 2015

(54) ECT2 PEPTIDES AND VACCINES INCLUDING THE SAME

(75) Inventors: Yusuke Nakamura, Tokyo (JP); Takuya Tsunoda, Kanagawa (JP); Ryuji Ohsawa, Kanagawa (JP); Sachiko Yoshimura, Kanagawa (JP); Tomohisa Watanabe, Kanagawa (JP)

(73) Assignee: OncoTherapy Science, Inc., Kanagawa (JP)

( * ) Notice: Subject to any disclaimer, the term of this patent is extended or adjusted under 35 U.S.C. 154(b) by 0 days.

(21) Appl. No.: 13/638,272

(22) PCT Filed: Mar. 30, 2011

(86) PCT No.: PCT/JP2011/001909
§ 371 (c)(1),
(2), (4) Date: Dec. 24, 2012

(87) PCT Pub. No.: WO2011/122022
PCT Pub. Date: Oct. 6, 2011

(65) Prior Publication Data
US 2013/0095128 A1    Apr. 18, 2013

Related U.S. Application Data

(60) Provisional application No. 61/320,577, filed on Apr. 2, 2010.

(51) Int. Cl.
*A61K 38/08* (2006.01)
*A61K 38/10* (2006.01)
*A61K 38/00* (2006.01)
*A61K 38/04* (2006.01)
*C07K 7/06* (2006.01)
*A61K 39/00* (2006.01)

(52) U.S. Cl.
CPC .............. *C07K 7/06* (2013.01); *A61K 39/0011* (2013.01); *A61K 2039/572* (2013.01)
USPC ........ 514/21.6; 514/21.5; 514/19.2; 530/328; 530/327

(58) Field of Classification Search
None
See application file for complete search history.

(56) References Cited

U.S. PATENT DOCUMENTS

| | | | | |
|---|---|---|---|---|
| 7,227,007 | B2 * | 6/2007 | Matsuda et al. | 536/23.1 |
| 7,393,663 | B2 * | 7/2008 | Edwards et al. | 435/69.8 |
| 7,998,695 | B2 | 8/2011 | Nakamura et al. | |
| 8,053,183 | B2 | 11/2011 | Nakamura et al. | |
| 2003/0013649 | A1 | 1/2003 | Rosen et al. | |
| 2003/0082758 | A1 | 5/2003 | Rosen et al. | |
| 2003/0092616 | A1 | 5/2003 | Matsuda et al. | |
| 2009/0208514 | A1 | 8/2009 | Nakamura et al. | |
| 2009/0317392 | A1 | 12/2009 | Nakamura et al. | |
| 2010/0040641 | A1 | 2/2010 | Tsunoda et al. | |
| 2010/0061933 | A1 | 3/2010 | Kimura | |
| 2011/0319280 | A1 | 12/2011 | Nakamura et al. | |
| 2012/0014996 | A1 | 1/2012 | Nakamura et al. | |
| 2012/0021946 | A1 | 1/2012 | Nakamura et al. | |

FOREIGN PATENT DOCUMENTS

| | | |
|---|---|---|
| CN | 101589059 | 11/2009 |
| EP | 2105511 A1 | 9/2009 |
| JP | 2004-518413 A | 6/2004 |
| JP | 2005-506833 A | 3/2005 |
| JP | 2009-502116 A | 1/2009 |
| WO | 02/30963 A1 | 4/2002 |
| WO | 02/078524 A2 | 10/2002 |
| WO | 02/096943 A1 | 12/2002 |
| WO | 02/099062 A2 | 12/2002 |
| WO | 2005/019258 A2 | 3/2005 |
| WO | 2005/019475 A2 | 3/2005 |
| WO | 2006/085684 A2 | 8/2006 |
| WO | 2007/013665 A2 | 2/2007 |
| WO | 2007/013671 A2 | 2/2007 |
| WO | 2007/150077 A2 | 12/2007 |
| WO | 2008/047914 A1 | 4/2008 |
| WO | 2008/102557 A1 | 8/2008 |

(Continued)

OTHER PUBLICATIONS

Wells, 1990, Biochemistry 29:8509- 8517.*
Ngo et al., 1994, The Protein Folding Problem and Tertiary Structure Prediction, pp. 492-495.*
Tokuriki et al., 2009, Curr. Opin. Struc. Biol. 19:596-604.*
Shen et al. 2012, Cancer Immunol. Immunother., 62:393-403.*
Xu et al., 2012. Vaccine, 30, 2805-2810, 2012.*
Rosenberg et al. (2004. Nat. Med. 10:909-915.*
Leggatt et al J Immunology 161: 4728-4735, 1998.*

(Continued)

*Primary Examiner* — Shulamith H Shafer
(74) *Attorney, Agent, or Firm* — Kilpatrick Townsend & Stockton LLP

(57) ABSTRACT

Isolated peptides derived from SEQ ID NO: 42 and fragments thereof that bind to an HLA antigen and induce cytotoxic T lymphocytes (CTL) and thus are suitable for use in the context of cancer immunotherapy, more particularly cancer vaccines, are described herein. The inventive peptides encompass both the afore-mentioned amino acid sequences and modified versions thereof, in which one, two, or several amino acids are substituted, deleted, inserted or added, provided such modified versions retain the requisite HLA binding and/or CTL inducibility of the original sequences. Further provided are nucleic acids encoding any of the aforementioned peptides as well as pharmaceutical agents, substances and/or compositions that include or incorporate any of the aforementioned peptides or nucleic acids. The peptides, nucleic acids, pharmaceutical agents, substances and compositions of this invention find particular utility in the treatment of cancers and tumors, including, for example, bladder cancer, breast cancer, cervical cancer, cholangiocellular carcinoma, CML, colorectal cancer, esophageal cancer, NSCLC, lymphoma, pancreatic cancer, prostate cancer, renal carcinoma and SCLC.

16 Claims, 3 Drawing Sheets

(56) References Cited

FOREIGN PATENT DOCUMENTS

| WO | 2010/007791 A1 | 1/2010 |
|---|---|---|
| WO | 2010/021111 A1 | 2/2010 |

OTHER PUBLICATIONS

Adams, et al., "Prediction of binding to MHC class I molecules," *J Immunol Methods*, vol. 185(2), pp. 181-190 (Sep. 25, 1995).

Belli, et al., Vaccination of Metastatic Melanoma Patients With Autologous Tumor-Derived Heat Shock Protein gp96-Peptide Complexes: Clinical and Immunologic Findings, *J Clin Oncol.*, vol. 20(20), pp. 4169-4180 (Oct. 15, 2002).

Boon, "Tumor Antigens Recognized by Cytolytic T Lymphocytes: Present Perspectives for Specific Immunotherapy," *Int J Cancer*, vol. 54(2), pp. 177-180 (May 8, 1993).

Boon, et al., "Human Tumor Antigens Recognized by T Lymphocytes," *J Exp Med.*, vol. 183(3), pp. 725-729 (Mar. 1, 1996).

Butterfield, et al., "Generation of Human T-cell Responses to an HLA-A2.1-restricted Peptide Epitope Derived from α—Fetoprotein," *Cancer Res.*, vol. 59(13), pp. 3134-3142 (Jul. 1, 1999).

Coulie, et al., "Cytolytic T-cell responses of cancer patients vaccinated with a MAGE antigen," *Immunol Rev.* vol. 188, pp. 33-42 (Oct. 2002).

Dionne, et al., "Her-2/neu altered peptide ligant-induced CTL responses: implications for peptides with increased HLA affinity and T-cell-receptor interaction," *Cancer Immunol Immunother.*, vol. 53(4), pp. 307-314 (Epub Nov. 5, 2003, Apr. 2004).

Eguchi, et al., "RB silencing compromises the DNA damage-induced G2/M checkpoint and causes deregulated expression of the ECT2 oncogene," *Oncogene*, vol. 26(4), pp. 509-520 (Epub Jul. 24, 2006, Jan. 25, 2007).

Falk, et al., "Allele-specific motifs revealed by sequencing of self-peptides eluted from MHC molecules," *Nature*, vol. 351(6324), pp. 290-296 (May 23, 1991).

Fujie, et al., "A Mage-1-Encoded HLA-A24-Binding Synthetic Peptide Induces Specific Anti-Tumor Cytotoxic T Lymphocytes," *Int J Cancer*, vol. 80(2), pp. 169-172 (Jan. 18, 1999).

Gross, et al., "High vaccination efficiency of low-affinity epitopes in antitumor immunotherapy," *J Clin Invest.*, vol. 113(3), pp. 425-433 (Feb. 2004).

Hara, et al., Cytokinesis regulator ECT2 changes its conformation through phosphorylation at Thr-341 in G2/M phase, *Oncogene*, vol. 25(4), pp. 566-578 (Jan. 26, 2006).

Harada, et al., "Kinesin superfamily protein-derived peptides with the ability to induce glioma-reactive cytotoxic T lymphocytes in human leukocyte antigen-A24+ glioma patients," *Oncol Rep.*, vol. 17(3), pp. 629-636 (Mar. 2007).

Harris, "Structure and Function of the p53 Tumor Suppressor Gene: Clues for Rational Cancer Therapeutic Strategies," *J Natl Cancer Inst.*, vol. 88(20), pp. 1442-1455 (Oct. 16, 1996).

Hirata, et al., "Involvement of Epithelial Cell Transforming Sequence-2 Oncoantigen in Lung and Esophageal Cancer Progression," *Clin Cancer Res.*, vol. 15(1), pp. 256-266 (Jan. 1, 2009).

Hirata, et al., "Involvement of ECT2 Oncoantigen in Lung and Esophageal Cancer Progression," *Proceedings of 68th Annual Meeting of the Japanese Cancer Association*, vol. 68, p. 61, 0-104 (2009).

Hoffmann, et al., "The Ability of Variant Peptides to Reverse the Nonresponsiveness of T Lymphocytes to the Wild Type Sequence p53$_{264-272}$ Epitope," *J Immunol.*, vol. 168(3), pp. 1338-1347 (Feb. 1, 2002).

Kikuchi, et al., "Identification of a Sart-1-Derived Peptide Capable of Inducing HLA-A24-Restricted and Tumor-Specific Cytotoxic T Lymphocytes," *Int J Cancer*, vol. 81(3), pp. 459-466 (May 5, 1999).

Kim, et al., "The Tandem BRCT Domains of Ect2 Are Required for Both Negative and Positive Regulation of Ect2 in Cytokinesis," *J Biol Chem.*, vol. 280(7), pp. 5733-5739 (Epub Nov. 15, 2004, Feb. 18, 2005).

Kondo, et al., "Prominent Roles of Secondary Anchor Residues in Peptide Binding to HLA-A24 Human Class I Molecules," *J Immunol.*, vol. 155(9), pp. 4307-4312 (Nov. 1, 1995).

Kubo, et al., "Definition of Specific Peptide Motifs for Four Major HLA-A Alleles," *J Immunol.*, vol. 152(8), pp. 3913-3924 (Apr. 15, 1994).

Kuzushima, et al., "Efficient identification of HLA-A *2402-restricted cytomegalovirus-specific CD8+ T-cell epitopes by a computer algorithm and an enzyme-linked immunospot assay," *Blood.*, vol. 98(6), pp. 1872-1881 (Sep. 15, 2001).

Miki, "Interaction of Ect2 and Dbl with Rho-Related GTPases," *Methods Enzymo.*, vol. 256, pp. 90-98 (1995).

Miki, et al., "Oncogene ect2 is related to regulators of small GTP-binding proteins," *Nature*, vol. 362(6419), pp. 462-465 (Apr. 1, 1993).

Oiso, et al., "A Newly Identified MAGE-3-Derived Epitope Recognized by HLA-A24-Restricted Cytotoxic T Lymphocytes," *Int J Cancer*, vol. 81(3), pp. 387-394 (May 5, 1999).

Parker, et al., "Scheme for Ranking Potential HLA-A2 Binding Peptides Based on Independent Binding of Individual Peptide Side-Chains," *J Immunol.*, vol. 152(1), pp. 163-175 (Jan. 1, 1994).

Petronczki, et al., "Polo-like Kinase 1 Triggers the Initiation of Cytokinesis in Human Cells by Promoting Recruitment of the RhoGEF Ect2 to the Central Spindle," *Dev Cell*, vol. 12(5), pp. 713-725 (May 2007).

Rammensee, et al., "MHC ligands and peptide motifs: first listing," *Immunogenetics*, vol. 41(4), pp. 178-228 (1995).

Rosenberg, et al., "Cancer immunotherapy: moving beyond current vaccines," *Nat Med.*, vol. 10(9), pp. 909-915 (Sep. 2004).

Saito, et al., "Rho Exchange Factor ECT2 Is Induced by Growth Factors and Regulates Cytokinesis Through the N-Terminal Cell Cycle Regulator-Related Domains," *J Cell Biochem.*, vol. 90(4), pp. 819-836 (Nov. 1, 2003).

Sano, et al., "Expression level of ECT2 proto-oncogene correlates with prognosis in glioma patients," *Oncol Rep.*, vol. 16(5), pp. 1093-1098 (Nov. 2006).

Schueler, et al., "Structure-based prediction of binding peptides to MHC class I molecules: Application to a broad range of MHC alleles," *Protein Sci.*, vol. 9(9), pp. 1838-1846 (Sep. 2000).

Scoumanne, et al., "The Epithelial Cell Transforming Sequence 2, a Guanine Nucleotide Exchange Factor for Rho GTPases, Is Repressed by p53 via Protein Methyltransferases and Is Required for $G_1$-S Transition," *Cancer Res.*, vol. 66(12), pp. 6271-6279 (Jun. 15, 2006).

Suda, et al., "Identification of *secernin 1* as a novel immunotherapy target for gastric cancer using the expression profiles of cDNA microarray," *Cancer Sci.*, vol. 97(5), pp. 411-419 (May 2006).

Tanaka, et al., "Induction of Antitumor Cytotoxic T Lymphocytes with a MAGE-3-encoded Synthetic Peptide Presented by Human Leukocytes Antigen-A24," *Cancer Res.*, vol. 57(20), pp. 4465-4468 (Oct. 15, 1997).

Tatsumoto, et al., "Human ECT2 Is an Exchange Factor for Rho GTPases, Phosphorylated in G2/M Phases, and Involved in Cytokinesis," *J Cell Biol.*, vol. 147(5), pp. 921-927 (Nov. 29, 1999).

Tsunoda, "Novel DC Therapy Using Epitope Peptides," *Biotherapy*, vol. 18(6), pp. 503-509 (Nov. 2004).

Van Der Burg, et al., "Immunogenicity of Peptides Bound to MHC Class I Molecules Depends on the MHC-Peptide Complex Stability," *J Immunol.*, vol. 156(9), pp. 3308-3314 (May 1, 1996).

Vissers, et al., "The Renal Cell Carcinoma-associated Antigen G250 Encodes a Human Leukocyte Antigen (HLA)-A2.1-restricted Epitope Recognized by Cytotoxic T Lymphocytes," *Cancer Res.*, vol. 59(21), pp. 5554-5559 (Nov. 1, 1999).

Yamabuki, et al., "Isolation and characterization of a novel gene IMS-ES01 as a therapeutic target for esophageal squamous-cell carcinoma," *Proceedings of the 64th Annual Meeting of the Japanese Cancer Association*, 64, p. 525, W-821 (2005).

Yen, et al., "Copy number changes of target genes in chromosome 3q25.3-qter of esophageal squamous cell carcinoma: TP63 is amplified in early carcinogenesis but down-regulated as diseases progressed," *World J Gastroenterol*, vol. 11(9), pp. 1267-1272 (Mar. 7, 2005).

(56) References Cited

OTHER PUBLICATIONS

Zaremba, et al., "Identification of an Enhancer Agonist Cytotoxic T Lymphocyte Peptide from Human Carcinoembryonic Antigen," *Cancer Res.*, vol. 57(20), pp. 4570-4577 (Oct. 15, 1997).
U.S. Appl. No. 13/464,831, filed May 4, 2012, 162 pages.
U.S. Appl. No. 13/536,327, filed Jun. 28, 2012, 204 pages.
International Search Report and Written Opinion for PCT/JP2011/001909, mailed May 10, 2011, 10 pages.
Dionne, et al., "Functional characterization of CTL against gp100 altered peptide ligands," *Cancer Immunol Immunother.*, vol. 52(4), pp. 199-206 (Apr. 2003).
U.S. Appl. No. 13/744,354, filed Jan. 17, 2013, 124 pages.
Fields, et al., "The guanine nucleotide exchange factor (GEF) Ect2 is an oncogene in human cancer," *Adv Enzyme Regul.*, vol. 50(1), pp. 190-200 (Epub Nov. 6, 2009).
Strausberg, et al., GenBank Accession No. AAI68962.1, downloaded from http://www.ncbi.nlm.nih.gov/protein/AAI68962.1, 2 pages (Mar. 18, 2009).
Ishazaki et al., "Inhibition of Tumor Growth with Antiangiogenic Cancer Vaccine Using Epitope Peptides Derived from Human Vascular Endothelial Growth Factor Receptor 1," *Clin Cancer Res* 2006;12(19) Oct. 1, 2006.
U.S. Appl. No. 14/079,144, filed Nov. 13, 2013, 159 pages.
U.S. Appl. No. 14/274,373, filed May 9, 2014, 123 pages.
GenBank Accession No. AAQ83675.1, "Epithelial Cell Transforming 2 [*Homo sapiens*]," Sep. 29, 2003.

* cited by examiner a.

b.

SEQUENCE LISTING

```
<160> NUMBER OF SEQ ID NOS: 46

<210> SEQ ID NO 1
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 1

Leu Leu Ile Gly Ser Thr Ser Tyr Val
1               5

<210> SEQ ID NO 2
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 2

Gln Ile Phe Asp Val Val Tyr Glu Val
1               5

<210> SEQ ID NO 3
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 3
```

Phe Leu Phe Asn Asp Cys Leu Glu Ile
1               5

<210> SEQ ID NO 4
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 4

Thr Leu Phe Leu Phe Asn Asp Cys Leu
1               5

<210> SEQ ID NO 5
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 5

Leu Leu Ser Ser His Arg Ser Leu Val
1               5

<210> SEQ ID NO 6
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 6

Met Met Asn Leu Val Leu Cys Phe Thr
1               5

<210> SEQ ID NO 7
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 7

Leu Leu Ile Arg Pro Val Gln Arg Leu
1               5

<210> SEQ ID NO 8
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 8

Val Val Thr Asp Phe Gln Asp Ser Val
1               5

<210> SEQ ID NO 9
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 9

Leu Leu Asn Asp Leu Lys Lys His Thr

```
<210> SEQ ID NO 10
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 10

Phe Gln Asp Cys Ile Leu Ser Phe Leu
1               5

<210> SEQ ID NO 11
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 11

Phe Glu Pro Ser Lys Lys Leu Tyr Val
1               5

<210> SEQ ID NO 12
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 12

Ala Leu Met Thr Ser His Gly Ser Val
1               5

<210> SEQ ID NO 13
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 13

Asn Glu Gln Asp Phe Tyr Ala Ala Val
1               5

<210> SEQ ID NO 14
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 14

Met Leu Cys Arg His Val Ala Asn Thr
1               5

<210> SEQ ID NO 15
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 15

Ala Gln Leu Ser Arg Glu Thr Asp Val
1               5
```

```
<210> SEQ ID NO 16
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 16

Asn Ile Leu Ala Thr Ile Ile Gln Leu
1               5

<210> SEQ ID NO 17
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 17

Thr Leu Ser Arg Ser Thr Thr His Leu
1               5

<210> SEQ ID NO 18
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 18

Arg Leu Pro Ser Val Ala Leu Leu Leu
1               5

<210> SEQ ID NO 19
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 19

Thr Leu Val His His Met Gly Gly Val
1               5

<210> SEQ ID NO 20
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 20

Ile Ile Gln Leu Phe Gln Val Pro Leu
1               5

<210> SEQ ID NO 21
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 21

Asn Leu Leu Ile Gly Ser Thr Ser Tyr Val
1               5                   10
```

<210> SEQ ID NO 22
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 22

Asn Leu Leu Ser Ser His Arg Ser Leu Val
1               5                   10

<210> SEQ ID NO 23
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 23

Ser Met Met Asn Leu Val Leu Cys Phe Thr
1               5                   10

<210> SEQ ID NO 24
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 24

Leu Met Pro Leu Ser Gln Ile Lys Lys Val
1               5                   10

<210> SEQ ID NO 25
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 25

Lys Met Leu Cys Arg His Val Ala Asn Thr
1               5                   10

<210> SEQ ID NO 26
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 26

Ser Leu Val Glu Leu Leu Ile Arg Pro Val
1               5                   10

<210> SEQ ID NO 27
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 27

Thr Gln Gly Glu Lys Phe Arg Val Ala Val
1               5                   10

```
<210> SEQ ID NO 28
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 28

Tyr Thr Ala Asp Pro Glu Ser Phe Glu Val
1               5                   10

<210> SEQ ID NO 29
<211> LENGTH: 10
<212> TYPE: PRT
<213> ORGANISM: Artificial Sequence
<220> FEATURE:
<223> OTHER INFORMATION: ELYQtESNYV

<400> SEQUENCE: 29

Glu Leu Tyr Gln Thr Glu Ser Asn Tyr Val
1               5                   10

<210> SEQ ID NO 30
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 30

Lys Gln Ile Phe Asp Val Val Tyr Glu Val
1               5                   10

<210> SEQ ID NO 31
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 31

Phe Val Val Thr Asp Phe Gln Asp Ser Val
1               5                   10

<210> SEQ ID NO 32
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 32

Ser Ile Phe Asp Ser Lys Val Thr Glu Ile
1               5                   10

<210> SEQ ID NO 33
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 33

Leu Leu Leu Asn Asp Leu Lys Lys His Thr
1               5                   10

<210> SEQ ID NO 34
```

```
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 34

Ile Leu Ala Pro Glu Glu Ile Lys Thr Ile
1               5                   10

<210> SEQ ID NO 35
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 35

Phe Leu Phe Asn Asp Cys Leu Glu Ile Ala
1               5                   10

<210> SEQ ID NO 36
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 36

Leu Leu Asn Asp Leu Lys Lys His Thr Ala
1               5                   10

<210> SEQ ID NO 37
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 37

Tyr Gln Thr Glu Ser Asn Tyr Val Asn Ile
1               5                   10

<210> SEQ ID NO 38
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 38

Asp Leu Val Lys Thr Tyr Pro Pro Phe Val
1               5                   10

<210> SEQ ID NO 39
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 39

Phe Gly Ser Ile Pro Asp Ile Phe Asp Val
1               5                   10

<210> SEQ ID NO 40
<211> LENGTH: 10
```

```
<212> TYPE: PRT
<213> ORGANISM: Artificial Sequence
<220> FEATURE:
<223> OTHER INFORMATION: An artificially synthesized peptide sequence

<400> SEQUENCE: 40

Gly Leu Asp Ser Pro Glu Phe Glu Asn Val
1               5                   10

<210> SEQ ID NO 41
<211> LENGTH: 4349
<212> TYPE: DNA
<213> ORGANISM: Homo sapiens

<400> SEQUENCE: 41
tttttgaatc ggttgtggcg gccgcggcga ggaatggcgg tatttgtgag aggagtcggc      60
gtttgaagag gtggaactcc tagggctttt ttgagagtga cggagtctac ctcttgttac     120
ctagactgga gtgcagtggc acgatctcgg ctcactgcaa cctctgcctc ccgggttcaa     180
gcgattctcc tgcctcagcc tcctgagtag ctgggattac aggtgcctgc caccaagccc     240
agctaatttt tgtatttta gtagagatgg ggtttcattg tgttggccag gctggtctcg     300
aactcctgac ctcgtgatcc gcccgccttg gcctcccaaa gtgctaggat tacaagtgtg     360
agccaccgcg tccggccttt caaatggtat ttttgatttt cctcttccag tccttaaagc     420
agctgattta agaatacaa atcatggct gaaaatagtg tattaacatc cactactggg       480
aggactagct tggcagactc ttccattttt gattctaaag ttactgagat tccaaggaa      540
aacttactta ttgatctac ttcatatgta aagagatgc ctcagattga acaagagtg        600
atattggttc aagaagctgg aaaacaagaa gaactataa aagccttaaa ggacattaaa      660
gtgggctttg taaagatgga gtcagtgaa gaatttgaag gtttggattc tccggaattt      720
gaaaatgtat ttgtagtcac ggactttcag gattctgtct taatgaccct ctacaaggct    780
gattgtagag ttattggacc accagttgta ttaaattgtt cacaaaaagg agagcctttg    840
ccatttcat gtcgcccgtt gtattgtaca agtatgatga tctagtact atgctttact      900
ggatttagga aaaagaga actagtcagg ttggtgacat tggtccatca catgggtgga      960
gttattcgaa aagactttaa ttcaaaagtt acacatttgg tggcaaattg tacacaagga   1020
gaaaattca gggttgctgt gagtctaggt actccaatta tgaagccaga atggatttat    1080
aaagctggg aaaggcggaa tgaacaggat ttctatgcag cagttgatga ctttagaaat    1140
gaatttaaag ttcctccatt tcaagattgt atttaagtt tcctgggatt ttcagatgaa    1200
gagaaaacca atatggaaga atgactgaa atgcaaggag gtaaatattt accgcttgga    1260
gatgaaagat gcactcacct tgtagttgaa gagaatatag taaagatct tcccttgaa     1320
ccttcaaaga aactttatgt tgtcaagcaa gagtggttct ggggaagcat tcaaatggat   1380
gcccgagctg gagaaactat gtatttatat gaaaaggcaa atactcctga gctcaagaaa   1440
tcagtgtcaa tgctttctct aaataccct aacagcaatc gcaaacgacg tcgtttaaaa    1500
gaaacacttg ctcagctttc aagagagaca gacgtgtcac cattccacc ccgtaagcgc    1560
ccatcagctg agcattccct ttccataggg tcactcctag atatctccaa cacaccagag   1620
tctagcatta actatggaga cacccccaaag tcttgtacta agtcttctaa aagctccact   1680
ccagttcctt caaagcagtc agcaaggtgg caagttgcaa aagagcttta tcaaactgaa   1740
agtaattatg ttaatatatt ggcaacaatt attcagttat ttcaagtacc attggaagag   1800
gaaggacaac gtggtggacc tatccttgca ccagaggaga ttaagactat ttttggtagc   1860
```

```
atcccagata tctttgatgt acacactaag ataaaggatg atcttgaaga ccttatagtt    1920
aattgggatg agagcaaaag cattggtgac attttctga aatattcaaa agatttggta     1980
aaaacctacc ctcccttgt aaacttcttt gaatgagca aggaaacaat tattaaatgt      2040
gaaaaacaga aaccaagatt tcatgctttt ctcaagataa accaagcaaa accagaatgt    2100
ggacggcaga gccttgttga acttcttatc cgaccagtac agaggttacc cagtgttgca    2160 ttactttta atgatcttaa gaagcataca gctgatgaaa atccagacaa aagcacttta    2220 gaaaagcta ttggatcact gaaggaagta atgacgcata ttaatgagga taagagaaaa    2280
acagaagctc aaaagcaaat ttttgatgtt gtttatgaag tagatggatg cccagctaat    2340
cttttatctt ctcaccgaag cttagtacag cgggttgaaa caatttctct aggtgagcac    2400
ccctgtgaca gaggagaaca agtaactctc ttcctcttca atgattgcct agagatagca    2460
agaaaacggc acaaggttat tggcactttt aggagtcctc atggccaaac ccgaccccca    2520
gcttctctta agcatattca cctaatgcct ctttctcaga ttaagaaggt attggacata    2580
agagagacag aagattgcca taatgctttt gccttgcttg tgaggccacc aacagagcag    2640
gcaaatgtgc tactcagttt ccagatgaca tcagatgaac ttccaaaaga aaactggcta    2700
aagatgctgt gtcgacatgt agctaacacc atttgtaaag cagatgctga aatcttatt    2760 tatactgctg atccagaatc ctttgaagta aatacaaaag atatggacag tacattgagt    2820
agagcatcaa gagcaataaa aaagacttca aaaaaggtta caagagcatt ctctttctcc    2880
aaaactccaa aaagagctct tcgaagggct cttatgacat cccacggctc agtggaggga    2940
agaagtcctt ccagcaatga taagcatgta atgagtcgtc tttctagcac atcatcatta    3000
gcaggtatcc cttctcccctc cttgtcagc cttccttcct tctttgaaag gagaagtcat    3060
acgttaagta gatctacaac tcatttgata tgaagcgtta ccaaaatctt aaattataga    3120
aatgtataga cacctcatac tcaaataaga aactgactta aatggtactt gtaattagca    3180
cgttggtgaa agctggaagg aagataaata acactaaact atgctatttg atttttcttc    3240
ttgaaagagt aaggtttacc tgttacattt tcaagttaat tcatgtaaaa aatgatagtg    3300
attttgatgt aatttatctc ttgttgaat ctgtcattca aaggccaata atttaagttg    3360
ctatcagctg atattagtag cttgcaacc ctgatagagt aaataaattt tatgggtggg    3420
tgccaaatac tgctgtgaat ctatttgtat agtatccatg aatgaattta tggaaataga    3480
tatttgtgca gctcaattta tgcagagatt aaatgacatc ataatactgg atgaaaactt    3540
gcatagaatt ctgattaaat agtgggtctg tttcacatgt gcagtttgaa gtatttaaat    3600
aaccactcct ttcacagttt attttcttct caagcgtttt caagatctag catgtggatt    3660
ttaaaagatt tgccctcatt aacaagaata acatttaaag gagattgttt caaaatattt    3720
ttgcaaattg agataaggac agaaagattg agaaacattg tatattttgc aaaaacaaga    3780
tgtttgtagc tgtttcagag agagtacggt atatttatgg taatttatc cactagcaaa    3840 tcttgattta gttgatagt cgtcgtcgga attttatttt gaaggataag accatgggaa    3900
aattgtggta aagactgttt gtaccttca tgaaataatt ctgaagttgc catcagtttt    3960
actaatcttc tgtgaaatgc atagatatgc gcatgttcaa cttttattg tggtcttata    4020 attaaatgta aaattgaaaa ttcatttgct gtttcaaagt gtgatatctt tcacaatagc    4080
ctttttatag tcagtaattc agaataatca agttcatatg gataaatgca tttttatttc    4140
```

```
ctatttcttt agggagtgct acaaatgttt gtcacttaaa tttcaagttt ctgttttaat      4200
agttaactga ctatagattg ttttctatgc catgtatgtg ccacttctga gagtagtaaa      4260
tgactctttg ctacatttta aaagcaattg tattagtaag aactttgtaa ataaatacct      4320
aaaacccaag tgtaaaaaaa aaaaaaaaa                                        4349

<210> SEQ ID NO 42
<211> LENGTH: 882
<212> TYPE: PRT
<213> ORGANISM: Homo sapiens

<400> SEQUENCE: 42

Met Ala Glu Asn Ser Val Leu Thr Ser Thr Thr Gly Arg Thr Ser Leu
1               5                   10                  15

Ala Asp Ser Ser Ile Phe Asp Ser Lys Val Thr Glu Ile Ser Lys Glu
            20                  25                  30

Asn Leu Leu Ile Gly Ser Thr Ser Tyr Val Glu Glu Met Pro Gln Ile
        35                  40                  45

Glu Thr Arg Val Ile Leu Val Gln Glu Ala Gly Lys Gln Glu Glu Leu
    50                  55                  60

Ile Lys Ala Leu Lys Asp Ile Lys Val Gly Phe Val Lys Met Glu Ser
65                  70                  75                  80

Val Glu Glu Phe Glu Gly Leu Asp Ser Pro Glu Phe Glu Asn Val Phe
                85                  90                  95

Val Val Thr Asp Phe Gln Asp Ser Val Phe Asn Asp Leu Tyr Lys Ala
            100                 105                 110

Asp Cys Arg Val Ile Gly Pro Pro Val Val Leu Asn Cys Ser Gln Lys
        115                 120                 125

Gly Glu Pro Leu Pro Phe Ser Cys Arg Pro Leu Tyr Cys Thr Ser Met
    130                 135                 140

Met Asn Leu Val Leu Cys Phe Thr Gly Phe Arg Lys Lys Glu Glu Leu
145                 150                 155                 160

Val Arg Leu Val Thr Leu Val His His Met Gly Gly Val Ile Arg Lys
                165                 170                 175

Asp Phe Asn Ser Lys Val Thr His Leu Val Ala Asn Cys Thr Gln Gly
            180                 185                 190

Glu Lys Phe Arg Val Ala Val Ser Leu Gly Thr Pro Ile Met Lys Pro
        195                 200                 205

Glu Trp Ile Tyr Lys Ala Trp Glu Arg Arg Asn Glu Gln Asp Phe Tyr
    210                 215                 220

Ala Ala Val Asp Asp Phe Arg Asn Glu Phe Lys Val Pro Pro Phe Gln
225                 230                 235                 240

Asp Cys Ile Leu Ser Phe Leu Gly Phe Ser Asp Glu Glu Lys Thr Asn
                245                 250                 255

Met Glu Glu Met Thr Glu Met Gln Gly Gly Lys Tyr Leu Pro Leu Gly
            260                 265                 270

Asp Glu Arg Cys Thr His Leu Val Val Glu Asn Ile Val Lys Asp
        275                 280                 285

Leu Pro Phe Glu Pro Ser Lys Lys Leu Tyr Val Val Lys Gln Glu Trp
    290                 295                 300

Phe Trp Gly Ser Ile Gln Met Asp Ala Arg Ala Gly Glu Thr Met Tyr
305                 310                 315                 320
```

-continued

```
Leu Tyr Glu Lys Ala Asn Thr Pro Glu Leu Lys Lys Ser Val Ser Met
                325                 330                 335

Leu Ser Leu Asn Thr Pro Asn Ser Asn Arg Lys Arg Arg Arg Leu Lys
            340                 345                 350

Glu Thr Leu Ala Gln Leu Ser Arg Glu Thr Asp Val Ser Pro Phe Pro
        355                 360                 365

Pro Arg Lys Arg Pro Ser Ala Glu His Ser Leu Ser Ile Gly Ser Leu
370                 375                 380

Leu Asp Ile Ser Asn Thr Pro Glu Ser Ser Ile Asn Tyr Gly Asp Thr
385                 390                 395                 400

Pro Lys Ser Cys Thr Lys Ser Ser Lys Ser Ser Thr Pro Val Pro Ser
                405                 410                 415

Lys Gln Ser Ala Arg Trp Gln Val Ala Lys Glu Leu Tyr Gln Thr Glu
            420                 425                 430

Ser Asn Tyr Val Asn Ile Leu Ala Thr Ile Ile Gln Leu Phe Gln Val
        435                 440                 445

Pro Leu Glu Glu Glu Gly Gln Arg Gly Gly Pro Ile Leu Ala Pro Glu
450                 455                 460

Glu Ile Lys Thr Ile Phe Gly Ser Ile Pro Asp Ile Phe Asp Val His
465                 470                 475                 480

Thr Lys Ile Lys Asp Asp Leu Glu Asp Leu Ile Val Asn Trp Asp Glu
                485                 490                 495

Ser Lys Ser Ile Gly Asp Ile Phe Leu Lys Tyr Ser Lys Asp Leu Val
            500                 505                 510

Lys Thr Tyr Pro Pro Phe Val Asn Phe Phe Glu Met Ser Lys Glu Thr
        515                 520                 525

Ile Ile Lys Cys Glu Lys Gln Lys Pro Arg Phe His Ala Phe Leu Lys
530                 535                 540

Ile Asn Gln Ala Lys Pro Glu Cys Gly Arg Gln Ser Leu Val Glu Leu
545                 550                 555                 560

Leu Ile Arg Pro Val Gln Arg Leu Pro Ser Val Ala Leu Leu Leu Asn
                565                 570                 575

Asp Leu Lys Lys His Thr Ala Asp Glu Asn Pro Asp Lys Ser Thr Leu
            580                 585                 590

Glu Lys Ala Ile Gly Ser Leu Lys Glu Val Met Thr His Ile Asn Glu
        595                 600                 605

Asp Lys Arg Lys Thr Glu Ala Gln Lys Gln Ile Phe Asp Val Val Tyr
610                 615                 620

Glu Val Asp Gly Cys Pro Ala Asn Leu Leu Ser Ser His Arg Ser Leu
625                 630                 635                 640

Val Gln Arg Val Glu Thr Ile Ser Leu Gly Glu His Pro Cys Asp Arg
                645                 650                 655

Gly Glu Gln Val Thr Leu Phe Leu Phe Asn Asp Cys Leu Glu Ile Ala
            660                 665                 670

Arg Lys Arg His Lys Val Ile Gly Thr Phe Arg Ser Pro His Gly Gln
        675                 680                 685

Thr Arg Pro Pro Ala Ser Leu Lys His Ile His Leu Met Pro Leu Ser
690                 695                 700

Gln Ile Lys Lys Val Leu Asp Ile Arg Glu Thr Glu Asp Cys His Asn
705                 710                 715                 720

Ala Phe Ala Leu Leu Val Arg Pro Pro Thr Glu Gln Ala Asn Val Leu
                725                 730                 735
```

```
Leu Ser Phe Gln Met Thr Ser Asp Glu Leu Pro Lys Glu Asn Trp Leu
            740                 745                 750

Lys Met Leu Cys Arg His Val Ala Asn Thr Ile Cys Lys Ala Asp Ala
        755                 760                 765

Glu Asn Leu Ile Tyr Thr Ala Asp Pro Glu Ser Phe Glu Val Asn Thr
770                 775                 780

Lys Asp Met Asp Ser Thr Leu Ser Arg Ala Ser Arg Ala Ile Lys Lys
785                 790                 795                 800

Thr Ser Lys Lys Val Thr Arg Ala Phe Ser Phe Ser Lys Thr Pro Lys
                805                 810                 815

Arg Ala Leu Arg Arg Ala Leu Met Thr Ser His Gly Ser Val Glu Gly
            820                 825                 830

Arg Ser Pro Ser Ser Asn Asp Lys His Val Met Ser Arg Leu Ser Ser
        835                 840                 845

Thr Ser Ser Leu Ala Gly Ile Pro Ser Pro Ser Leu Val Ser Leu Pro
    850                 855                 860

Ser Phe Phe Glu Arg Arg Ser His Thr Leu Ser Arg Ser Thr Thr His
865                 870                 875                 880

Leu Ile

<210> SEQ ID NO 43
<211> LENGTH: 22
<212> TYPE: DNA
<213> ORGANISM: Artificial
<220> FEATURE:
<223> OTHER INFORMATION: Artificial sequence

<400> SEQUENCE: 43
gtctaccagg cattcgcttc at                                              22

<210> SEQ ID NO 44
<211> LENGTH: 24
<212> TYPE: DNA
<213> ORGANISM: Artificial
<220> FEATURE:
<223> OTHER INFORMATION: Artificial sequence

<400> SEQUENCE: 44
tcagctggac cacagccgca gcgt                                            24

<210> SEQ ID NO 45
<211> LENGTH: 21
<212> TYPE: DNA
<213> ORGANISM: Artificial
<220> FEATURE:
<223> OTHER INFORMATION: Artificial sequence

<400> SEQUENCE: 45
tcagaaatcc tttctcttga c                                               21

<210> SEQ ID NO 46
<211> LENGTH: 24
<212> TYPE: DNA
<213> ORGANISM: Artificial
<220> FEATURE:
<223> OTHER INFORMATION: Artificial sequence

<400> SEQUENCE: 46
ctagcctctg gaatcctttc tctt                                            24
```

ECT2 PEPTIDES AND VACCINES
INCLUDING THE SAME

PRIORITY

The present application is a U.S. National Phase of PCT/JP2011/001909, filed Mar. 30, 2011, which claims the benefit of U.S. Provisional Application No. 61/320,577, filed on Apr. 2, 2010, the contents of which are hereby incorporated herein by reference in their entirety for all purposes.

The present application claims the benefit of U.S. Provisional Application No. 61/320,577, filed on Apr. 2, 2010, the entire contents of which are incorporated by reference herein.

REFERENCE TO SEQUENCE LISTING

This application includes a Sequence Listing as a text file named "SEQTXT_87331-023310US-852216.txt" created Sep. 26, 2012, and containing 23,356 bytes. The material contained in this text file is incorporated by reference in its entirety for all purposes.

TECHNICAL FIELD

The present invention relates to the field of biological science, more specifically to the field of cancer therapy. In particular, the present invention relates to novel peptides that are extremely effective as cancer vaccines as well as drugs for treating and preventing tumors.

BACKGROUND ART

It has been demonstrated that CD8 positive CTLs recognize epitope peptides derived from tumor-associated antigens (TAAs) found on the major histocompatibility complex (MHC) class I molecule, and then kill the tumor cells. Since the discovery of the melanoma antigen (MAGE) family as the first example of TAAs, many other TAAs have been discovered through immunological approaches (NPL 1, Boon T, Int J Cancer 1993 May 8, 54(2): 177-80; NPL 2, Boon T & van der Bruggen P, J Exp Med 1996 Mar. 1, 183(3): 725-9). Some of these TAAs are currently undergoing clinical development as immunotherapeutic targets.

Favorable TAAs are indispensable for the proliferation and survival of cancer cells. The use of such TAAs as targets for immunotherapy may minimize the well-described risk of immune escape of cancer cells attributable to deletion, mutation, or down-regulation of TAAs as a consequence of therapeutically driven immune selection. Accordingly, the identification of new TAAs capable of inducing potent and specific anti-tumor immune responses warrants further development and the clinical investigation of peptide vaccination strategies for various types of cancer is ongoing (NPL 3, Harris C C, J Natl Cancer Inst 1996 Oct. 16, 88(20): 1442-55; NPL 4, Butterfield L H et al., Cancer Res 1999 Jul. 1, 59(13): 3134-42; NPL 5, Vissers J L et al., Cancer Res 1999 Nov. 1, 59(21): 5554-9; NPL 6, van der Burg S H et al., J Immunol 1996 May 1, 156(9): 3308-14; NPL 7, Tanaka F et al., Cancer Res 1997 Oct. 15, 57(20): 4465-8; NPL 8, Fujie T et al., Int J Cancer 1999 Jan. 18, 80(2): 169-72; NPL 9, Kikuchi M et al., Int J Cancer 1999 May 5, 81(3): 459-66; NPL 10, Oiso M et al., Int J Cancer 1999 May 5, 81(3): 387-94). To date, several clinical trials using these tumor-associated antigen derived peptides have been reported. Unfortunately, many of the current cancer vaccine trial have shown only a low objective response rate (NPL 11, Belli F et al., J Clin Oncol 2002 Oct. 15, 20(20): 4169-80; NPL 12, Coulie P G et al., Immunol Rev 2002 October, 188: 33-42; NPL 13, Rosenberg S A et al., Nat Med 2004 September, 10(9): 909-15). Accordingly, there remains a need for new TAAs as immunotherapeutic targets.

Epithelial cell transforming sequence 2 (ECT2) oncogene (GenBank Accession No. AY376439; e.g., SEQ ID No: 41) has been discovered from the transcripts identified as up-regulated in cancer. The ECT2 gene is specifically up-regulated in the tumor cells of various cancers, including, but not limited to, bladder cancer, breast cancer, cervical cancer, cholangiocellular carcinoma, chronic myeloid leukemia (CML), colorectal cancer, esophageal cancer, non-small cell lung cancer (NSCLC), lymphoma, pancreatic cancer, prostate cancer, renal carcinoma and small cell lung cancer (SCLC) and thus is of particular to the present invention (PTL 1, WO2007/013671; PTL 2, WO2008/102557; PTL 3, WO2010/007791). In particular, immunogenic peptides derived from ECT2 may find utility in selectively killing tumor cells that express such antigens.

CITATION LIST

Non Patent Literature

[NPL 1] Boon T, Int J Cancer 1993 May 8, 54(2): 177-80
[NPL 2] Boon T & van der Bruggen P, J Exp Med 1996 Mar. 1, 183(3): 725-9
[NPL 3] Harris C C, J Natl Cancer Inst 1996 Oct. 16, 88(20): 1442-55
[NPL 4] Butterfield L H et al., Cancer Res 1999 Jul. 1, 59(13): 3134-42
[NPL 5] Vissers J L et al., Cancer Res 1999 Nov. 1, 59(21): 5554-9
[NPL 6] van der Burg S H et al., J Immunol 1996 May 1, 156(9): 3308-14
[NPL 7] Tanaka F et al., Cancer Res 1997 Oct. 15, 57(20): 4465-8
[NPL 8] Fujie T et al., Int J Cancer 1999 Jan. 18, 80(2): 169-72
[NPL 9] Kikuchi M et al., Int J Cancer 1999 May 5, 81(3): 459-66
[NPL 10] Oiso M et al., Int J Cancer 1999 May 5, 81(3): 387-94
[NPL 11] Belli F et al., J Clin Oncol 2002 Oct. 15, 20(20): 4169-80
[NPL 12] Coulie P G et al., Immunol Rev 2002 October, 188: 33-42
[NPL 13] Rosenberg S A et al., Nat Med 2004 September, 10(9): 909-15

Patent Literature

[PTL 1] WO2007/013671
[PTL 2] WO2008/102557
[PTL 3] WO2010/007791

SUMMARY OF INVENTION

The present invention is based, at least in part, on the discovery of the suitable targets of immunotherapy. Because TAAs are generally perceived by the immune system as "self" and therefore often have no immunogenicity, the discovery of appropriate targets is of extreme importance. Recognizing that ECT2 (SEQ ID NO: 42 encoded by the gene of GenBank Accession No. AY376439 (for example, SEQ ID NO: 41)) has been identified as up-regulated in cancers, examples of which include, but are not limited to, bladder cancer, breast cancer, cervical cancer, cholangiocellular carcinoma, CML, colorectal cancer, esophageal cancer, NSCLC, lymphoma, pancreatic cancer, prostate cancer, renal carcinoma and SCLC, the present invention focuses on ECT2 as a candidate for the target of cancer/tumor immunotherapy, more particularly novel ECT2 epitope peptides that may serve as suitable immunotherapeutic targets.

To that end, the present invention is directed, at least in part, to the identification of specific epitope peptides among the gene products of ECT2 that possess the ability to induce CTLs specific to ECT2. As discussed in detail below, peripheral blood mononuclear cells (PBMCs) obtained from a healthy donor were stimulated using HLA-A*0201 binding candidate peptides derived from ECT2. CTL lines were then established with specific cytotoxicity against the HLA-A2 positive target cells pulsed with each of candidate peptides. The results herein demonstrate that these peptides are HLA-A2 restricted epitope peptides that may induce potent and specific immune responses against cells expressing ECT2. These results further demonstrate that ECT2 is strongly immunogenic and the epitopes thereof are effective targets for cancer/tumor immunotherapy.

Accordingly, it is an object of the present invention to provide isolated peptides binding to HLA antigen, including ECT2 (SEQ ID NO: 42) and the immunologically active fragments thereof. Such peptides are expected to have CTL inducibility and, thus, can be used to induce CTL ex vivo or to be administered to a subject for inducing immune responses against cancers, examples of which include, but are not limited to, bladder cancer, breast cancer, cervical cancer, cholangiocellular carcinoma, CML, colorectal cancer, esophageal cancer, NSCLC, lymphoma, pancreatic cancer, prostate cancer, renal carcinoma and SCLC. Preferred peptides are nonapeptides and decapeptides, more preferably, nonapeptides and decapeptides having the amino acid sequence selected from among SEQ ID NOs: 1 to 40. Peptides having an amino sequence selected among SEQ ID NOs: 1, 3 and 21 showed strong CTL inducibility and thus are particularly preferred.

The present invention also contemplates modified peptides having an amino acid sequence selected from among SEQ ID NOs: 1 to 40 in which one, two or more amino acids are substituted, inserted, deleted or added, so long as the modified peptides retain the requisite CTL inducibility of the original peptide.

The present invention further encompasses isolated polynucleotides that encode any of the peptides of the present invention. These polynucleotides can be used to induce or prepare APCs with CTL inducibility or, like the above-described peptides of the present invention, can be administered to a subject for inducing immune responses against cancers.

When administered to a subject, the present peptides are presented on the surface of APCs so as to induce CTLs targeting the respective peptides. Therefore, one object of the present invention is to provide agents, compositions and/or substances that include or incorporate any peptides or polynucleotides of the present invention for inducing CTLs. Such agents, compositions and substances can be used for the treatment and/or prophylaxis and/or post-operative recurrence of cancers, especially bladder cancer, breast cancer, cervical cancer, cholangiocellular carcinoma, CML, colorectal cancer, esophageal cancer, NSCLC, lymphoma, pancreatic cancer, prostate cancer, renal carcinoma and SCLC. Thus, it is yet another object of the present invention to provide pharmaceutical agents, compositions and/or substances for the treatment and/or prophylaxis and/or prevention of postoperative recurrence of cancer that include or incorporate one or more peptides or polynucleotides of the present invention. Instead of or in addition to the present peptides or polynucleotides, the pharmaceutical agents, compositions and substances of the present invention may include as active ingredients APCs or exosomes that present any of the present peptides.

The peptides or polynucleotides of the present invention may be used to induce APCs that present on the surface a complex of an HLA antigen and a present peptide, for example, by contacting APCs derived from a subject with the peptide or introducing a polynucleotide encoding a peptide of the present invention into APCs. Such APCs have high CTL inducibility against target peptides and find use in cancer immunotherapy. Accordingly, the present invention encompasses the methods for inducing APCs with CTL inducibility as well as APCs obtained by such methods.

It is a further object of the present invention to provide a method for inducing CTL, such methods including the step of co-culturing CD8 positive cells with APCs or exosomes presenting the peptide of the present invention on its surface or the step of introducing a gene that includes a polynucleotide encoding a T cell receptor (TCR) subunit polypeptide binding to the present peptide. CTLs obtained by such methods find use in the treatment and/or prevention of cancers, examples of which include, but are not limited to, bladder cancer, breast cancer, cervical cancer, cholangiocellular carcinoma, CML, colorectal cancer, esophageal cancer, NSCLC, lymphoma, pancreatic cancer, prostate cancer, renal carcinoma and SCLC. Therefore, it is yet another object of the present invention to provide CTLs obtained by the present methods.

It is yet another object of the present invention to provide methods for inducing an immune response against cancer in a subject in need thereof, such methods including the step of administering compositions or substances including the ECT2 polypeptides or immunologically active fragments thereof, polynucleotides encoding ECT2 polypeptides, exosomes or the APCs presenting ECT2 polypeptides.

The applicability of the present invention extends to any of a number of diseases relating to or arising from ECT2 overexpression, such as cancer, examples of which include, but are not limited to, bladder cancer, breast cancer, cervical cancer, cholangiocellular carcinoma, CML, colorectal cancer, esophageal cancer, NSCLC, lymphoma, pancreatic cancer, prostate cancer, renal carcinoma and SCLC.

More specifically, the present invention provides followings:

[1] An isolated peptide consisting of the amino acid sequence of SEQ ID NO: 42 or an immunologically active fragment thereof, wherein said peptide binds an HLA antigen and induces cytotoxic T lymphocytes (CTLs),

[2] The isolated peptide of [1], wherein the HLA antigen is HLA-A2,

[3] The isolated peptide of [1] or [2], wherein said peptide comprises an amino acid sequence selected from the group consisting of SEQ ID NOs: 1 to 40,

[4] An isolated peptide selected from the group consisting of:

(a) an isolated peptide that binds to an HLA antigen and induces cytotoxic T lymphocytes (CTL) and consists of the amino acid sequence of SEQ ID NO: 42 or an immunologically active fragment thereof, (b) the isolated peptide of (a), wherein the HLA antigen is HLA-A2, (c) the isolated peptide of (a) or (b), which comprises an amino acid sequence selected from the group consisting of SEQ ID NOs: 1 to 40, and (d) the isolated peptide of (a) or (b) consisting of an amino acid sequence selected from the group consisting of SEQ ID NOs: 1 to 40, wherein 1, 2, or several amino acid(s) are substituted, deleted, inserted or added, provided said modified peptide retains the CTL inducibility of the original peptide,

[5] The isolated peptide of [4], which consists of an amino acid sequence selected from the group consisting of SEQ ID NOs: 1 to 40, wherein the peptide has one or both of the following characteristics:

(a) the second amino acid from the N-terminus is selected from the group consisting of leucine or methionine; and (b) the C-terminal amino acid is selected from the group consisting of valine or leucine,

[6] The isolated peptide of any one of [1] to [5], wherein said peptide is nonapeptide or decapeptide,

[7] An isolated polynucleotide encoding the peptide of any one of [1] to [6],

[8] A composition for inducing CTL, wherein the composition comprises one or more peptide(s) of any one of [1] to [6], or one or more polynucleotide(s) of [7],

[9] A pharmaceutical composition for the treatment and/or prophylaxis and/or prevention of postoperative recurrence of cancer, wherein the composition comprises one or more peptide(s) of any one of [1] to [6], or one or more polynucleotides of [7],

[10] The pharmaceutical composition of [9], wherein said composition is formulated for the administration to a subject whose HLA antigen is HLA-A2,

[11] The pharmaceutical composition of [9] or [10], wherein said composition is formulated for the treatment of cancer,

[12] A method for inducing an antigen-presenting cell (APC) with CTL inducibility comprising a step selected from the group consisting of:

(a) contacting an APC with a peptide of any one of [1] to [6] in vitro, ex vivo or in vivo, and (b) introducing a polynucleotide encoding the peptide of any one of [1] to [6] into an APC,

[13] A method for inducing CTL by a method that comprises a step selected from the group consisting of:

(a) co-culturing CD8 positive T cells with APCs that present on the surface a complex of an HLA antigen and the peptide of any one of [1] to [6];

(b) co-culturing CD8 positive T cells with exosomes that present on the surface a complex of an HLA antigen and a peptide of any one of [1] to [6]; and (c) introducing a gene that comprises a polynucleotide encoding a T cell receptor (TCR) subunit polypeptide bound to a peptide of any one of [1] to [6] into a T cell,

[14] An isolated APC that presents on its surface a complex of an HLA antigen and the peptide of any one of [1] to [6],

[15] The APC of [14], which is induced by the method of [12],

[16] An isolated CTL that targets any of the peptides of [1] to [6],

[17] A CTL of [16], induced by the method of [13],

[18] A method of inducing an immune response against cancer in a subject in need thereof, said method comprising the step of administering to the subject a composition comprising a peptide of [1] to [6], an immunologically active fragment thereof, or a polynucleotide encoding the peptide or the fragment,

[19] An antibody or immunologically active fragment thereof against any of the peptides of [1] to [6],

[20] A vector comprising a nucleotide sequence encoding any of the peptides of [1] to [6],

[21] A diagnostic kit comprising any of the peptides of [1] to [6], the nucleotide of [7] or the antibody of [19].

It is to be understood that both the foregoing summary of the present invention and the following detailed description are of exemplified embodiments, and not restrictive of the present invention or other alternate embodiments of the present invention.

In addition to the above, other objects and features of the invention will become more fully apparent when the following detailed description is read in conjunction with the accompanying figures and examples. However, it is to be understood that both the foregoing summary of the invention and the following detailed description are of exemplified embodiments, and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF DRAWINGS

Various aspects and applications of the present invention will become apparent to the skilled artisan upon consideration of the brief description of the figures and the detailed description of the present invention and its preferred embodiments which follows.

DESCRIPTION OF EMBODIMENTS

Figure 1:
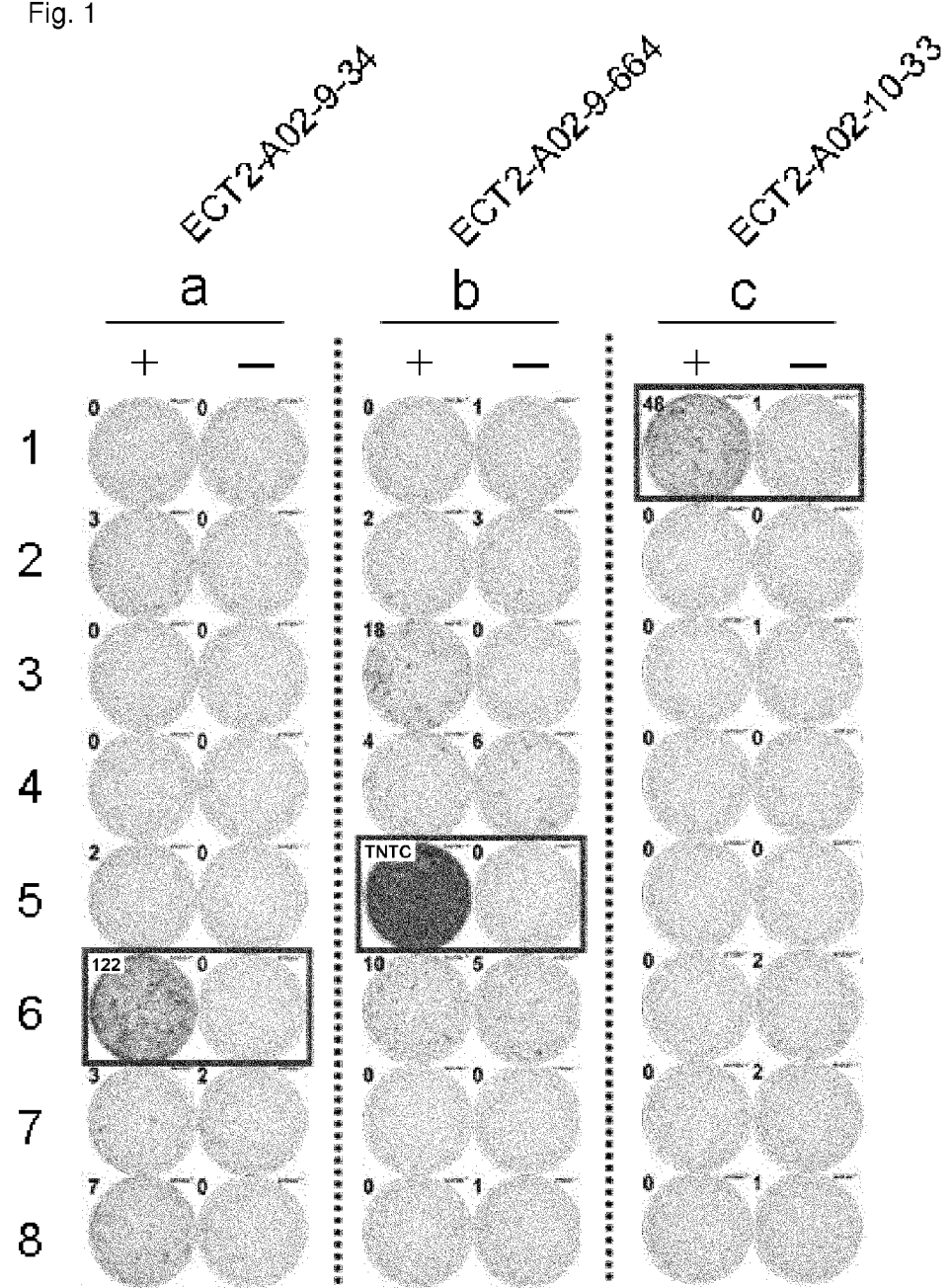
FIG. 1 is composed of a series of photographs, (a) to (c), depicting the results of IFN-gamma ELISPOT assays on CTLs that were induced with peptides derived from ECT2. The CTLs in well number #6 stimulated with ECT2-A02-9-34 (SEQ ID NO: 1) (a), in well number #5 stimulated with ECT2-A02-9-664 (SEQ ID NO: 3) (b) and in well number #1 stimulated with ECT2-A02-10-33 (SEQ ID NO: 21) (c) showed potent IFN-gamma production as compared with the control. The square on the well of these pictures indicates that the cells from corresponding well were expanded to establish CTL lines. In the figures, "+" indicates the IFN-gamma production against target cells pulsed with the appropriate peptide, and "−" indicates the IFN-gamma production against target cells not pulsed with any peptides.

Although any methods and materials similar or equivalent to those described herein can be used in the practice or testing of embodiments of the present invention, the preferred materials, methods, and devices are now described. However, before the present materials and methods are described, it should be understood that these descriptions are merely illustrative only and not intended to be limiting. It should also be understood that the present invention is not limited to the particular sizes, shapes, dimensions, materials, methodologies, protocols, etc. described herein, as these may vary in accordance with routine experimentation and/or optimization. Furthermore, the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue or prior invention.

Unless otherwise defined, all technical and scientific terms used herein have the same meaning as commonly understood by one of ordinary skill in the art to which the present invention belongs. In case of conflict, the present specification, including definitions, will control. In addition, the materials, methods, and examples are illustrative only and not intended to be limiting.

I. DEFINITIONS

The words "a", "an", and "the" as used herein mean "at least one" unless otherwise specifically indicated.

The terms "polypeptide", "peptide" and "protein" are used interchangeably herein to refer to a polymer of amino acid residues. The terms apply to amino acid polymers in which one or more amino acid residue(s) may be modified residue(s), or non-naturally occurring residue(s), such as artificial chemical mimetic(s) of corresponding naturally occurring amino acid(s), as well as to naturally occurring amino acid polymers.

The term "oligopeptide" sometimes used in the present specification is used to refer to peptides of the present invention which are 20 residues or fewer, typically 15 residues or fewer in length and is typically composed of between about 8 and about 11 residues, often 9 or 10 residues.

The term "amino acid" as used herein refers to naturally occurring and synthetic amino acids, as well as amino acid analogs and amino acid mimetics that similarly function to the naturally occurring amino acids. Amino acid may be either L-amino acids or D-amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have one or more modified R group(s) or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotides", "nucleotides" and "nucleic acids" are used interchangeably herein and, unless otherwise specifically indicated are similarly to the amino acids referred to by their commonly accepted single-letter codes.

The terms "agent", "substance" and "composition" as used interchangeably herein to refer to a product that includes the specified ingredients in the specified amounts, as well as any product that results, directly or indirectly, from combination of the specified ingredients in the specified amounts. Such terms, when used in relation to the modifier "pharmaceutical" (e.g., "pharmaceutical agent" and "pharmaceutical composition") are intended to encompass a product that include the active ingredient(s), and any inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, in the context of the present invention, the terms "pharmaceutical agent" and "pharmaceutical composition" refer to any product made by admixing a molecule or compound of the present invention and a pharmaceutically or physiologically acceptable carrier.

The phrase "pharmaceutically acceptable carrier" or "physiologically acceptable carrier", as used herein, means a pharmaceutically or physiologically acceptable material, composition, substance or vehicle, including but not limited to, a liquid or solid filler, diluent, excipient, solvent or encapsulating material, involved in carrying or transporting the subject scaffolded polypharmacophores from one organ, or portion of the body, to another organ, or portion of the body.

The pharmaceutical agents or compositions of the present invention find particular use as vaccines. In the context of the present invention, the phrase "vaccine" (also referred to as an "immunogenic composition") refers to a substance that has the function to induce anti-tumor immunity upon inoculation into animals.

The term "active ingredient" herein refers to a substance in an agent or composition that is biologically or physiologically active. Particularly, in the context of a pharmaceutical agent or composition, the term "active ingredient" refers to a substance that shows an objective pharmacological effect. For example, in case of pharmaceutical agents or compositions for use in the treatment or prevention of cancer, active ingredients in the agents or compositions may lead to at least one biological or physiological action on cancer cells and/or tissues directly or indirectly. Preferably, such action may include reducing or inhibiting cancer cell growth, damaging or killing cancer cells and/or tissues, and so on. Typically, indirect effect of active ingredients is inductions of CTLs recognizing or killing cancer cells. Before being formulated, the "active ingredient" may also be referred to as "bulk", "drug substance" or "technical product".

Unless otherwise defined, the term "cancer" refers to the cancers overexpressing ECT2 gene, examples of which include, but are not limited to, bladder cancer, breast cancer, cervical cancer, cholangiocellular carcinoma, CML, colorectal cancer, esophageal cancer, NSCLC, lymphoma, pancreatic cancer, prostate cancer, renal carcinoma and SCLC.

Unless otherwise defined, the terms "cytotoxic T lymphocyte", "cytotoxic T cell" and "CTL" are used interchangeably herein and unless otherwise specifically indicated, refer to a sub-group of T lymphocytes that are capable of recognizing non-self cells (e.g., tumor/cancer cells, virus-infected cells) and inducing the death of such cells.

Unless otherwise defined, the term "HLA-A2", as used herein, representatively refers to the subtypes examples of which include, but are not limited to, HLA-A*0201, HLA-A*0202, HLA-A*0203, HLA-A*0204, HLA-A*0205, HLA-A*0206, HLA-A*0207, HLA-A*0210, HLA-A*0211, HLA-A*0213, HLA-A*0216, HLA-A*0218, HLA-A*0219, HLA-A*0228 and HLA-A*0250.

Unless otherwise defined, the term "kit" as used herein, is used in reference to a combination of reagents and other materials. It is contemplated herein that the kit may include microarray, chip, marker, and so on. It is not intended that the term "kit" be limited to a particular combination of reagents and/or materials.

As used herein, in the context of a subject or patient, the phrase "HLA-A2 positive" refers to that the subject or patient homozygously or heterozygously possess HLA-A2 antigen gene, and HLA-A2 antigen is expressed in cells of the subject or patient as an HLA antigen.

To the extent that the methods and compositions of the present invention find utility in the context of the "treatment" of cancer, a treatment is deemed "efficacious" if it leads to clinical benefit such as, reduction in expression of ECT2 gene, or a decrease in size, prevalence, or metastatic potential of the cancer in the subject. When the treatment is applied prophylactically, "efficacious" means that it retards or prevents cancers from forming or prevents or alleviates a clinical symptom of cancer. Efficaciousness is determined in association with any known method for diagnosing or treating the particular tumor type.

To the extent that the methods and compositions of the present invention find utility in the context of the "prevention" and "prophylaxis" of cancer, such terms are interchangeably used herein to refer to any activity that reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis can include a wide range of prophylactic therapies aimed at alleviating the severity of the particular disorder, e.g. reducing the proliferation and metastasis of tumors.

In the context of the present invention, the treatment and/or prophylaxis of cancer and/or the prevention of postoperative recurrence thereof include any of the following steps, such as the surgical removal of cancer cells, the inhibition of the growth of cancerous cells, the involution or regression of a tumor, the induction of remission and suppression of occurrence of cancer, the tumor regression, and the reduction or inhibition of metastasis. Effective treatment and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

In the context of the present invention, the term "antibody" refers to immunoglobulins and fragments thereof that are specifically reactive to a designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an antibody herein is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity. An "antibody" indicates all classes (e.g. IgA, IgD, IgE, IgG and IgM).

Unless otherwise defined, all technical and scientific terms used herein have the same meaning as commonly understood by one of ordinary skill in the art to which the present invention belongs.

II. PEPTIDES

To demonstrate that peptides derived from ECT2 function as an antigen recognized by CTLs, peptides derived from ECT2 (SEQ ID NO: 42) were analyzed to determine whether they were antigen epitopes restricted by HLA-A2 which are commonly encountered HLA alleles (Date Y et al., Tissue Antigens 47: 93-101, 1996; Kondo A et al., J Immunol 155: 4307-12, 1995; Kubo R T et al., J Immunol 152: 3913-24, 1994).

Candidates of HLA-A2 binding peptides derived from ECT2 were identified based on their binding affinities to HLA-A2. The following candidate peptides were identified:
ECT2-A2-9-34 (SEQ ID NO: 1),
ECT2-A2-9-619 (SEQ ID NO: 2),
ECT2-A2-9-664 (SEQ ID NO: 3),
ECT2-A2-9-662 (SEQ ID NO: 4),
ECT2-A2-9-634 (SEQ ID NO: 5),
ECT2-A2-9-145 (SEQ ID NO: 6),
ECT2-A2-9-561 (SEQ ID NO: 7),
ECT2-A2-9-98 (SEQ ID NO: 8),
ECT2-A2-9-575 (SEQ ID NO: 9),
ECT2-A2-9-240 (SEQ ID NO: 10),
ECT2-A2-9-292 (SEQ ID NO: 11),
ECT2-A2-9-823 (SEQ ID NO: 12),
ECT2-A2-9-220 (SEQ ID NO: 13),
ECT2-A2-9-755 (SEQ ID NO: 14),
ECT2-A2-9-357 (SEQ ID NO: 15),
ECT2-A2-9-438 (SEQ ID NO: 16),
ECT2-A2-9-874 (SEQ ID NO: 17),
ECT2-A2-9-568 (SEQ ID NO: 18),
ECT2-A2-9-166 (SEQ ID NO: 19), ECT2-A2-9-443 (SEQ ID NO: 20),
ECT2-A2-10-33 (SEQ ID NO: 21),
ECT2-A2-10-633 (SEQ ID NO: 22),
ECT2-A2-10-144 (SEQ ID NO: 23),
ECT2-A2-10-701 (SEQ ID NO: 24),
ECT2-A2-10-754 (SEQ ID NO: 25),
ECT2-A2-10-557 (SEQ ID NO: 26),
ECT2-A2-10-191 (SEQ ID NO: 27),
ECT2-A2-10-774 (SEQ ID NO: 28),
ECT2-A2-10-428 (SEQ ID NO: 29),
ECT2-A2-10-618 (SEQ ID NO: 30),
ECT2-A2-10-97 (SEQ ID NO: 31),
ECT2-A2-10-20 (SEQ ID NO: 32),
ECT2-A2-10-574 (SEQ ID NO: 33)
ECT2-A2-10-461 (SEQ ID NO: 34),
ECT2-A2-10-664 (SEQ ID NO: 35),
ECT2-A2-10-575 (SEQ ID NO: 36),
ECT2-A2-10-430 (SEQ ID NO: 37),
ECT2-A2-10-511 (SEQ ID NO: 38),
ECT2-A2-10-471 (SEQ ID NO: 39) and
ECT2-A2-10-87 (SEQ ID NO: 40).

Moreover, after in vitro stimulation of T-cells by dendritic cells (DCs) pulsed (loaded) with these peptides, CTLs were successfully established by stimulating the DCs with each of the following peptides;
ECT2-A2-9-34 (SEQ ID NO: 1),
ECT2-A2-9-664 (SEQ ID NO: 3) and
ECT2-A2-10-33 (SEQ ID NO: 21).

These established CTLs showed potent specific CTL activity against target cells pulsed with respective peptides. These results demonstrate that ECT2 is an antigen recognized by CTLs and that the peptides tested are epitope peptides of ECT2 restricted by HLA-A2.

Since the ECT2 gene is over expressed in cancer cells such as bladder cancer, breast cancer, cervical cancer, cholangiocellular carcinoma, CML, colorectal cancer, esophageal cancer, NSCLC, lymphoma, pancreatic cancer, prostate cancer, renal carcinoma and SCLC and not expressed in most normal organs, it is a good target for cancer immunotherapy. Thus, the present invention provides nonapeptides (peptides composed of nine amino acid residues) and decapeptides (peptides composed of ten amino acid residues) of CTL-recognized epitopes from ECT2. Alternatively, the present invention provides isolated peptides which bind to HLA antigens and induce cytotoxic T lymphocytes (CTLs), wherein the peptide has the amino acid sequence of SEQ ID NO: 42 or is an immunologically active fragment thereof. More specifically, in some embodiments, the present invention provides peptides having an amino acid sequence selected from among SEQ ID NOs: 1 to 40.

Generally, software programs now available, for example, on the Internet, such as those described in Parker K C et al., J Immunol 1994 Jan. 1, 152(1): 163-75 and Nielsen M et al., Protein Sci 2003; 12: 1007-17 can be used to calculate the binding affinities between various peptides and HLA antigens in silico. Binding affinity with HLA antigens can be measured as described, for example, in Parker K C et al., J Immunol 1994 Jan. 1, 152(1): 163-75, Kuzushima K et al., Blood 2001, 98(6): 1872-81, Larsen M V et al. BMC Bioinformatics. 2007 Oct. 31; 8: 424, Buus S et al. Tissue Antigens., 62:378-84, 2003, Nielsen M et al., Protein Sci 2003; 12: 1007-17, and Nielsen M et al. PLoS ONE 2007; 2: e796, which are summarized in, e.g., Lafuente E M et al., Current Pharmaceutical Design, 2009, 15, 3209-3220. Methods for determining binding affinity are described, for example, in the Journal of Immunological Methods (1995, 185: 181-190) and Protein Science (2000, 9: 1838-1846). Therefore, one can use such software programs to select those fragments derived from ECT2 that have high binding affinity with HLA antigens. Accordingly, the present invention encompasses peptides composed of any fragments derived from ECT2, which would be determined to bind with HLA antigens by such known programs. Furthermore, such peptides may include the peptide composed of the full length of ECT2.

The peptides of the present invention, particularly the nonapeptides and decapeptides of the present invention, may be flanked with additional amino acid residues so long as the peptides retain their CTL inducibility. The particular additional amino acid residues may be composed of any kind of amino acids so long as they do not impair the CTL inducibility of the original peptide. Thus, the present invention encompasses peptides having a binding affinity for HLA antigens, including peptides derived from ECT2. Such peptides are, for example, less than about 40 amino acids, often less than about 20 amino acids, usually less than about 15 amino acids.

Generally, it is known that modifications of one or more amino acids in a peptide do not influence the function of the peptide, or in some cases even enhance the desired function of the original protein. In fact, modified peptides (i.e., peptides composed of an amino acid sequence modified by substituting, deleting, inserting and/or adding one, two or several amino acid residues to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, according to one embodiment of the present invention, the peptide having CTL inducibility of the present invention may be composed of a peptide having an amino acid sequence selected from among SEQ ID NOs: 1 to 40, wherein one, two or even more amino acids are added, inserted, deleted and/or substituted.

Those of skill in the art will recognize that individual additions deletions, insertions and/or substitutions to an amino acid sequence that alter a single amino acid or a small percentage of amino acids results in the conservation of the properties of the original amino acid side-chain; it is thus referred to as "conservative substitution" or "conservative modification", wherein the alteration of a protein results in a protein with similar functions. Conservative substitution tables providing functionally similar amino acids are well known in the art. Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic group containing side-chain (H, F, Y, W). In addition, the following eight groups each contain amino acids that are conservative substitutions for one another:
 1) Alanine (A), Glycine (G);
 2) Aspartic acid (D), Glutamic acid (E);
 3) Asparagine (N), Glutamine (Q);
 4) Arginine (R), Lysine (K);
 5) Isoleucine (I), Leucine (L), Methionine (M), Valine (V);
 6) Phenylalanine (F), Tyrosine (Y), Tryptophan (W);
 7) Serine (S), Threonine (T); and
 8) Cysteine (C), Methionine (M) (see, e.g., Creighton, Proteins 1984).

Such conservatively modified peptides are also considered to be peptides of the present invention. However, the peptide of the present invention is not restricted thereto and may include non-conservative modifications, so long as the resulting modified peptide retains the requisite CTL inducibility of the original peptide. Furthermore, the modified peptides should not exclude CTL inducible peptides of polymorphic variants, interspecies homologues, and alleles of ECT2.

Amino acid residues may be inserted, substituted or added to the peptides of the present invention or, alternatively, amino acid residues may be deleted therefrom to achieve a higher binding affinity. To retain the requisite CTL inducibility one preferably modifies (inserts, deletes, adds and/or substitutes) only a small number (for example, 1, 2 or several) or a small percentage of amino acids. Herein, the term "several" means 5 or fewer amino acids, for example, 4 or 3 or fewer. The percentage of amino acids to be modified may be, for example, 20% or less, preferably 15% or less, more preferably 10% or less even more preferably 1 to 5%.

When used in the context of cancer immunotherapy, the present peptides may be presented on the surface of a cell or exosome as a complex with an HLA antigen. Therefore, it is preferable to select peptides that not only induce CTLs but also possess high binding affinity to the HLA antigen. To that end, the peptides can be modified by deletion, substitution, insertion, and/or addition of the amino acid residues to yield a modified peptide having improved binding affinity. In addition to peptides that are naturally displayed, since the regularity of the sequences of peptides displayed by binding to HLA antigens has already been known (J Immunol 1994, 152: 3913; Immunogenetics 1995, 41: 178; J Immunol 1994, 155: 4307), modifications based on such regularity may be introduced into the immunogenic peptides of the present invention.

For example, peptides exhibiting high HLA-A2 binding affinity tend to have the second amino acid from the N-terminus substituted with leucine or methionine. Likewise, peptides in which the C-terminal amino acid is substituted with valine or leucine can also be favorably used. Thus, peptides having an amino acid sequence selected from among SEQ ID NOs: 1 to 40, wherein the second amino acid from the N-terminus of the amino acid sequence of said SEQ ID NO is substituted with leucine or methionine, and peptides, and/or wherein the C-terminus of the amino acid sequence of said SEQ ID NO is substituted with valine or leucine are contemplated by the present invention.

Substitutions may be introduced not only at the terminal amino acids but also at the position of potential T cell receptor (TCR) recognition of peptides. Several studies have demonstrated that a peptide with amino acid substitutions may have equal to or better function than that of the original, for example, CAP1, $p53_{(264-272)}$, Her-2/neu$_{(369-377)}$ or gp100$_{(209-217)}$ (Zaremba et al. Cancer Res. 57, 4570-4577, 1997, T. K. Hoffmann et al. J. Immunol. (2002) February 1; 168(3):1338-47., S. O. Dionne et al. Cancer Immunol immunother. (2003) 52: 199-206 and S. O. Dionne et al. Cancer Immunology, Immunotherapy (2004) 53, 307-314).

The present invention also contemplates the addition of one, two or several amino acids to the N and/or C-terminus of the present peptides. Such modified peptides exhibiting high HLA antigen binding affinity and retaining CTL inducibility are also included in the present invention. For example, the present invention provides an isolated peptide of less than 14, 13, 12, 11, or 10 amino acids in length comprising the amino acid sequence selected from the group consisting of:

(i) an amino acid sequence selected from the group consisting of SEQ ID NOs: 1 to 20, wherein 1, 2, or several amino acid(s) are substituted, wherein the peptide binds an HLA antigen and induces cytotoxic T lymphocytes, and (ii) the amino acid sequence of (i), wherein the amino acid sequence has one or both of the following characteristics:

(a) the second amino acid from the N-terminus of said SEQ ID NO is selected from the group consisting of leucine or methionine; and (b) the C-terminal amino acid of said SEQ ID NO is selected from the group consisting of valine or leucine.

Moreover, the present invention also provides an isolated peptide of less than 15, 14, 13, 12, or 11 amino acids in length comprising the amino acid sequence selected from the group consisting of:

(i) an amino acid sequence selected from the group consisting of SEQ ID NOs: 21 to 40, wherein 1, 2, or several amino acid(s) are substituted, wherein the peptide binds an HLA antigen and induces cytotoxic T lymphocytes, and (ii) the amino acid sequence of (i), wherein the amino acid sequence has one or both of the following characteristics:

(a) the second amino acid from the N-terminus of said SEQ ID NO is selected from the group consisting of leucine or methionine; and (b) the C-terminal amino acid of said SEQ ID NO is selected from the group consisting of valine or leucine.

These peptides are processed in APC to present a peptide of (i), (ii), (i'), and (ii') thereon, when these peptides are contacted with, or introduced in APC.

However, when the peptide sequence is identical to a portion of the amino acid sequence of an endogenous or exogenous protein having a different function, side effects such as autoimmune disorders or allergic symptoms against specific substances may be induced. Therefore, one can perform homology searches using available databases to avoid situations in which the sequence of the peptide matches the amino acid sequence of another protein. When it becomes clear from the homology searches that there exists not even a peptide with 1 or 2 amino acids difference to the objective peptide, the objective peptide may be modified in order to increase its binding affinity with HLA antigens, and/or increase its CTL inducibility without any danger of such side effects.

Although peptides having high binding affinity to the HLA antigens as described above are expected to be highly effective, the candidate peptides, which are selected according to the presence of high binding affinity as an indicator, are further examined for the presence of CTL inducibility. Herein, the phrase "CTL inducibility" indicates the ability of the peptide to induce CTLs when presented on antigen-presenting cells (APCs). Further, "CTL inducibility" includes the ability of the peptide to induce CTL activation, CTL proliferation, promote CTL lysis of target cells, and to increase CTL IFN-gamma production.

Confirmation of CTL inducibility is accomplished by inducing APCs carrying human MHC antigens (for example, B-lymphocytes, macrophages, and dendritic cells (DCs)), or more specifically DCs derived from human peripheral blood mononuclear leukocytes, and after stimulation with the peptides, mixing with CD8 positive cells, and then measuring the IFN-gamma produced and released by CTL against the target cells. As the reaction system, transgenic animals that have been produced to express a human HLA antigen (for example, those described in BenMohamed L, Krishnan R, Longmate J, Auge C, Low L, Primus J, Diamond D J, Hum Immunol 2000 August, 61(8): 764-79, Related Articles, Books, Linkout Induction of CTL response by a minimal epitope vaccine in HLA A*0201/DR1 transgenic mice: dependent on MHC (HLA) class II restricted T(H) response) can be used. For example, the target cells may be radiolabeled with $^{51}Cr$ and such, and cytotoxic activity may be calculated from radioactivity released from the target cells. Alternatively, it may be examined by measuring IFN-gamma produced and released by CTL in the presence of APCs that carry immobilized peptides, and visualizing the inhibition zone on the media using anti-IFN-gamma monoclonal antibodies.

As a result of examining the CTL inducibility of the peptides as described above, it was discovered that nonapeptides and decapeptides selected from among those peptides having an amino acid sequence selected from among SEQ ID NOs: 1 to 40 showed particularly high CTL inducibility as well as high binding affinity to an HLA antigen. Thus, these peptides are exemplified as preferred embodiments of the present invention.

Furthermore, homology analysis results demonstrated that such peptides do not share significant homology with peptides derived from any other known human gene products. This lowers the possibility of unknown or undesired immune responses when used for immunotherapy. Therefore, also from this aspect, these peptides are useful for eliciting immunity against ECT2 in cancer patients. Thus, the peptides of the present invention, preferably, peptides having an amino acid sequence selected from among SEQ ID NOs: 1 to 40 are contemplated by the present invention.

In addition to modification of the present peptides, discussed above, the peptides of the present invention may be linked to other peptides, so long as the resulting linked peptide retains the requisite CTL inducibility of the original peptide and, more preferably, also retain the requisite HLA binding thereof. Exemplary "other" peptides include: the peptides of the present invention or the CTL inducible peptides derived from other TAAs. The linkers between the peptides are well known in the art, for example, AAY (P. M. Daftarian et al., J Trans Med 2007, 5:26), AAA, NKRK (R. P. M. Sutmuller et al., J. Immunol. 2000, 165: 7308-7315) or K (S. Ota et al., Can Res. 62, 1471-1476, K. S. Kawamura et al., J. Immunol. 2002, 168: 5709-5715).

For example, non-ECT2 tumor associated antigen peptides also can be used substantially simultaneously to increase immune response via HLA class I and/or class II. It is well established that cancer cells can express more than one tumor associated gene. Accordingly, it is within the scope of routine experimentation for one of ordinary skill in the art to determine whether a particular subject expresses additional tumor associated genes, and then to include HLA class I and/or HLA class II binding peptides derived from the expression products of such genes in ECT2 compositions or vaccines of the present invention.

Examples of HLA class I and HLA class II binding peptides are known to those of ordinary skill in the art (for example, see Coulie, Stem Cells 13:393-403, 1995), and can be used in connection with the present invention in a like manner as those disclosed herein. One of ordinary skill in the art can prepare polypeptides including one or more ECT2 peptides and one or more of the non-ECT2 peptides, or nucleic acids encoding such polypeptides, using conventional molecular biology procedures.

The above-linked peptides are referred to herein as "polytopes", i.e., groups of two or more potentially immunogenic or immune response stimulating peptides that can be joined together in various arrangements (e.g., concatenated, overlapping). The polytope (or nucleic acid encoding the polytope) can be administered in accordance with standard immunization protocols, e.g., to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., Proc. Natl. Acad. Sci. USA 92(13):5845-5849, 1995; Gilbert et al., Nature Biotechnol. 15(12):1280-1284, 1997; Thomson et al., J. Immunol. 157(2):822-826, 1996; Tarn et al., J. Exp. Med. 171(1):299-306, 1990). Polytopes containing various numbers and combinations of epitopes can be prepared and tested for recognition by CTLs and for efficacy in increasing an immune response.

The peptides of the present invention may be further linked to other substances, so long as they retain the requisite CTL inducibility. Illustrative examples of such "other" substances include, but are not limited to, peptides, lipids, sugar and sugar chains, acetyl groups, natural and synthetic polymers, etc. The peptides may contain modifications such as glycosylation, side chain oxidation, or phosphorylation, so long as the modifications do not destroy the biological activity of the peptides as described herein. These kinds of modifications may be performed to confer additional functions (e.g., targeting function, and delivery function) or to stabilize the polypeptide.

For example, to increase the in vivo stability of a polypeptide, it is known in the art to introduce D-amino acids, amino acid mimetics or unnatural amino acids; this concept may also be adopted for the present polypeptides. The stability of a polypeptide may be assayed in a number of ways. For instance, peptidases and various biological media, such as human plasma and serum, can be used to test stability (see, e.g., Verhoef et al., Eur J Drug Metab Pharmacokin 1986, 11: 291-302).

Moreover, as noted above, among the modified peptides that are substituted, inserted, deleted or added by one, two or several amino acid residues, those having same or higher activity as compared to original peptides can be screened for or selected. The present invention, therefore, also provides the method of screening for or selecting modified peptides having same or higher activity as compared to originals. For example, the method may include steps of:

a: substituting, inserting, deleting or adding at least one amino acid residue of a peptide of the present invention, b: determining the activity of the peptide, and c: selecting the peptide having same or higher activity as compared to the original.

Herein, the activity may include MHC binding activity, APC or CTL inducibility and cytotoxic activity.

Herein, the peptides of the present invention may also be described as "ECT2 peptide(s)" or "ECT2 polypeptide(s)".

III. PREPARATION OF ECT2 PEPTIDES

The peptides of the present invention may be prepared using well known techniques. For example, the peptides may be prepared synthetically, by recombinant DNA technology or chemical synthesis. The peptides of the present invention may be synthesized individually or as longer polypeptides including two or more peptides. The peptides may be isolated, i.e., purified or isolated substantially free from other naturally occurring host cell proteins and fragments thereof, or any other chemical substances.

The peptides of the present invention may contain modifications, such as glycosylation, side chain oxidation, or phosphorylation, provided such modifications do not destroy the biological activity of the original peptides. Other illustrative modifications include incorporation of D-amino acids or other amino acid mimetics that may be used, for example, to increase the serum half life of the peptides.

A peptide of the present invention may be obtained through chemical synthesis based on the selected amino acid sequence. For example, conventional peptide synthesis methods that may be adopted for the synthesis include:
  (i) Peptide Synthesis, Interscience, New York, 1966;
  (ii) The Proteins, Vol. 2, Academic Press, New York, 1976;
  (iii) Peptide Synthesis (in Japanese), Maruzen Co., 1975;
  (iv) Basics and Experiment of Peptide Synthesis (in Japanese), Maruzen Co., 1985;
  (v) Development of Pharmaceuticals (second volume) (in Japanese), Vol. 14 (peptide synthesis), Hirokawa, 1991;
  (vi) WO99/67288; and
  (vii) Barany G. & Merrifield R. B., Peptides Vol. 2, "Solid Phase Peptide Synthesis", Academic Press, New York, 1980, 100-118.

Alternatively, the present peptides may be obtained adopting any known genetic engineering methods for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. Such vectors and host cells are also provided by the present invention. The host cell is then cultured to produce the peptide of interest. The peptide may also be produced in vitro adopting an in vitro translation system.

IV. POLYNUCLEOTIDES

The present invention provides polynucleotides which encode any of the afore-mentioned peptides of the present invention. These include polynucleotides derived from the natural occurring ECT2 gene (GenBank Accession No. AY376439 (for example, SEQ ID NO: 41)) and those having a conservatively modified nucleotide sequences thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon may be altered to any of the corresponding codons described without altering the encoded polypeptide. Such nucleic acid variations, referred to in the art as "silent variations", represent one species of conservatively modified variant. Every nucleic acid sequence described herein as encoding a peptide also describes every possible silent variation of the nucleic acid. One of skill in the art will readily recognize that each codon in a nucleic acid (except AUG, which is ordinarily the only codon for methionine, and TGG, which is ordinarily the only codon for tryptophan) may be modified to yield a functionally identical molecule. Accordingly, each disclosed peptide-encoding nucleotide sequence represents an implicit disclosure of the silent variations associated therewith.

The polynucleotide of the present invention may be composed of DNA, RNA, and derivatives thereof. As is well known in the art, a DNA molecule is suitably composed of bases such as the naturally occurring bases A, T, C, and G, and T is replaced by U in an RNA. One of skill will recognize that non-naturally occurring bases be included in polynucleotides, as well.

The polynucleotide of the present invention may encode multiple peptides of the present invention, with or without intervening amino acid sequences. For example, the intervening amino acid sequence may provide a cleavage site (e.g., enzyme recognition sequence) of the polynucleotide or the translated peptides. Furthermore, the polynucleotide may include any additional sequences to the coding sequence encoding the peptide of the present invention. For example, the polynucleotide may be a recombinant polynucleotide that includes regulatory sequences required for the expression of the peptide or may be an expression vector (plasmid) with marker genes and such. In general, such recombinant polynucleotides may be prepared by the manipulation of polynucleotides through conventional recombinant techniques using, for example, polymerases and endonucleases.

Both recombinant and chemical synthesis techniques may be used to produce the polynucleotides of the present invention. For example, a polynucleotide may be produced by insertion into an appropriate vector, which may be expressed when transfected into a competent cell. Alternatively, a polynucleotide may be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide may be synthesized using the solid phase techniques, as described in Beaucage S L & Iyer R P, Tetrahedron 1992, 48: 2223-311; Matthes et al., EMBO J. 1984, 3: 801-5.

V. EXOSOMES

The present invention further provides intracellular vesicles called exosomes, which present complexes formed between the peptides of the present invention and HLA antigens on their surface. Exosomes may be prepared, for example by using the methods detailed in Japanese Patent Application Kohyo Publications No. Hei 11-510507 and WO99/03499, and may be prepared using APCs obtained from patients who are subject to treatment and/or prevention. The exosomes of the present invention may be inoculated as vaccines, similarly to the peptides of the present invention.

The type of HLA antigens included in the complexes must match that of the subject requiring treatment and/or prevention. For example, for Japanese, HLA-A2, particularly HLA-A*0201, HLA-A*0202, HLA-A*0203, HLA-A*0204, HLA-A*0205, HLA-A*0206, HLA-A*0207, HLA-A*0210, HLA-A*0211, HLA-A*0213, HLA-A*0216, HLA-A*0218, HLA-A*0219, HLA-A*0228 and HLA-A*0250 are often appropriate. The use of A24 type or the A2 type that is highly expressed among the Japanese and Caucasian is favorable for obtaining effective results, and subtypes such as HLA-A*0201, HLA-A*0202, HLA-A*0203, HLA-A*0204, HLA-A*0205, HLA-A*0206, HLA-A*0207, HLA-A*0210, HLA-A*0211, HLA-A*0213, HLA-A*0216, HLA-A*0218, HLA-A*0219, HLA-A*0228 and HLA-A*0250 find use. Typically, in the clinic, the type of HLA antigen of the patient requiring treatment is investigated in advance, which enables appropriate selection of peptides having high levels of binding affinity to this antigen, or having CTL inducibility by antigen presentation. Furthermore, in order to obtain peptides showing high binding affinity and CTL inducibility, substitution, insertion, deletion, or addition of 1, 2, or several amino acids may be performed based on the amino acid sequence of the naturally occurring ECT2 partial peptide.

In case of using the A2 type HLA antigen for the exosome of the present invention, the peptides having a sequence of any one of SEQ ID NOs: 1 to 40 have particular utility.

VI. ANTIGEN-PRESENTING CELLS (APCS)

The present invention also provides isolated APCs that present complexes formed with HLA antigens and the peptides of the present invention on its surface. The APCs may be derived from patients who are subject to treatment and/or prevention, and may be administered as vaccines by themselves or in combination with other drugs including the peptides of the present invention, exosomes, or CTLs.

The APCs are not limited to a particular kind of cells and include dendritic cells (DCs), Langerhans cells, macrophages, B cells, and activated T cells, which are known to present proteinaceous antigens on their cell surface so as to be recognized by lymphocytes. Since DC is a representative APC having the strongest CTL inducing activity among APCs, DCs find use as the APCs of the present invention.

For example, the APCs of the present invention may be obtained by inducing DCs from peripheral blood monocytes and then contacting (stimulating) them with the peptides of the present invention in vitro, ex vivo or in vivo. When the peptides of the present invention are administered to the subjects, APCs that present the peptides of the present invention are induced in the body of the subject. Therefore, the APCs of the present invention may be obtained by collecting the APCs from the subject after administering the peptides of the present invention to the subject. Alternatively, the APCs of the present invention may be obtained by contacting APCs collected from a subject with the peptide of the present invention.

The APCs of the present invention may be administered to a subject for inducing immune response against cancer in the subject by themselves or in combination with other drugs including the peptides, exosomes or CTLs of the present invention. For example, the ex vivo administration may include steps of:
 a: collecting APCs from a first subject,
 b: contacting with the APCs of step a, with the peptide, and
 c: administering the APCs of step b to a second subject.

The first subject and the second subject may be the same individual, or may be different individuals. The APCs obtained by step b may be administered as a vaccine for treating and/or preventing cancer, examples of which include, but are not limited to, bladder cancer, breast cancer, cervical cancer, cholangiocellular carcinoma, CML, colorectal cancer, esophageal cancer, NSCLC, lymphoma, pancreatic cancer, prostate cancer, renal carcinoma and SCLC.

The present invention also provides a method or process for manufacturing a pharmaceutical composition for inducing APCs, wherein the method includes the step of admixing or formulating the peptide of the invention with a pharmaceutically acceptable carrier.

According to an aspect of the present invention, the APCs have a high level of CTL inducibility. In the term of "high level of CTL inducibility", the high level is relative to the level of that by APC contacting with no peptide or peptides which may not induce the CTL. Such APCs having a high level of CTL inducibility may be prepared by a method which includes the step of transferring a polynucleotide encoding the peptide of the present invention to APCs in vitro as well as the method mentioned above. The introduced genes may be in the form of DNAs or RNAs. Examples of methods for introduction include, without particular limitations, various methods conventionally performed in this field, such as lipofection, electroporation, or calcium phosphate method may be used. More specifically, it may be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene into APCs, the gene undergoes transcription, translation, and such in the cell, and then the obtained protein is processed by MHC Class I or Class II, and proceeds through a presentation pathway to present partial peptides.

VII. CYTOTOXIC T LYMPHOCYTES (CTLS)

A CTL induced against any of the peptides of the present invention strengthens the immune response targeting cancer cells in vivo and thus may be used as vaccines similar to the peptides. Thus, the present invention provides isolated CTLs that are specifically induced or activated by any of the present peptides.

Such CTLs may be obtained by (1) administering the peptide(s) of the present invention to a subject or (2) contacting (stimulating) subject-derived APCs, and CD8 positive cells, or peripheral blood mononuclear leukocytes in vitro with the peptide(s) of the present invention or (3) contacting CD8 positive cells or peripheral blood mononuclear leukocytes in vitro with the APCs or exosomes presenting a complex of an HLA antigen and the peptide on its surface or (4) introducing a gene that includes a polynucleotide encoding a T cell receptor (TCR) subunit binding to the peptide of the present invention. Such APCs or exosomes may be prepared by the methods described above and details of the method of (4) is described bellow in section "VIII. T cell receptor (TCR)".

The CTLs of the present invention may be derived from patients who are subject to treatment and/or prevention, and may be administered by themselves or in combination with other drugs including the peptides of the present invention or exosomes for the purpose of regulating effects. The obtained CTLs act specifically against target cells presenting the peptides of the present invention, for example, the same peptides used for induction. The target cells may be cells that endogenously express ECT2, such as cancer cells, or cells that are transfected with the ECT2 gene; and cells that present a peptide of the present invention on the cell surface due to stimulation by the peptide may also serve as targets of activated CTL attack.

VIII. T CELL RECEPTOR (TCR)

The present invention also provides a composition including nucleic acids encoding polypeptides that are capable of forming a subunit of a T cell receptor (TCR), and methods of using the same. The TCR subunits have the ability to form TCRs that confer specificity to T cells against tumor cells presenting ECT2. By using the known methods in the art, the nucleic acids of alpha- and beta-chains as the TCR subunits of the CTL induced with one or more peptides of the present invention may be identified (WO2007/032255 and Morgan et al., J Immunol, 171, 3288 (2003)). For example, the PCR method is preferred to analyze the TCR. The PCR primers for the analysis can be, for example, 5'-R primers (5'-gtctaccag-gcattcgcttcat-3') as 5' side primers (SEQ ID NO: 43) and 3-TRa-C primers (5'-tcagctggaccacagccgcagcgt-3') specific to TCR alpha chain C region (SEQ ID NO: 44), 3-TRb-C1 primers (5'-tcagaaatcctttctcttgac-3') specific to TCR beta chain C1 region (SEQ ID NO: 45) or 3-TRbeta-C2 primers (5'-ctagcctctggaatcctttctctt-3') specific to TCR beta chain C2 region (SEQ ID NO: 46) as 3' side primers, but not limited thereto. The derivative TCRs may bind target cells displaying the ECT2 peptide with high avidity, and optionally mediate efficient killing of target cells presenting the ECT2 peptide in vivo and in vitro.

The nucleic acids encoding the TCR subunits may be incorporated into suitable vectors, e.g., retroviral vectors. These vectors are well known in the art. The nucleic acids or the vectors including them usefully may be transferred into a T cell, for example, a T cell from a patient. Advantageously, the present invention provides an off-the-shelf composition allowing rapid modification of a patient's own T cells (or those of another mammal) to rapidly and easily produce modified T cells having excellent cancer cell killing properties.

The specific TCR is a receptor capable of specifically recognizing a complex of a peptide of the present invention and HLA molecule, giving a T cell specific activity against the target cell when the TCR is presented on the surface of the T cell. A specific recognition of the above complex may be confirmed by any known methods, and preferred methods include, for example, HLA multimer staining analysis using HLA molecules and peptides of the present invention, and ELISPOT assay. By performing the ELISPOT assay, it can be confirmed that a T cell expressing the TCR on the cell surface recognizes a cell by the TCR, and that the signal is transmitted intracellularly. The confirmation that the above-mentioned complex can give a T cell cytotoxic activity when the complex exists on the T cell surface may also be carried out by a known method. A preferred method includes, for example, the determination of cytotoxic activity against an HLA positive target cell, such as chromium release assay.

Also, the present invention provides CTLs which are prepared by transduction with the nucleic acids encoding the TCR subunits polypeptides that bind to the ECT2 peptide of, e.g., SEQ ID NOs: 1 to 40 in the context of HLA-A2.

The transduced CTLs are capable of homing to cancer cells in vivo, and may be expanded by well known culturing methods in vitro (e.g., Kawakami et al., J. Immunol., 142, 3452-3461 (1989)). The CTLs of the present invention may be used to form an immunogenic composition useful in treating or the prevention of cancer in a patient in need of therapy or protection (WO2006/031221).

IX. PHARMACEUTICAL SUBSTANCES OR COMPOSITIONS

Since ECT2 expression is specifically elevated in cancer such as bladder cancer, breast cancer, cervical cancer, cholangiocellular carcinoma, CML, colorectal cancer, esophageal cancer, NSCLC, lymphoma, pancreatic cancer, prostate cancer, renal carcinoma and SCLC compared with normal tissue, the peptides of or polynucleotides of the present invention may be used for the treatment and/or for the prophylaxis of cancer, and/or prevention of postoperative recurrence thereof. Thus, the present invention provides a pharmaceutical, substance or composition for the treatment and/or prophylaxis and/or prevention of postoperative recurrence of cancer, such agent, substance or composition including as an active ingredient one or more of the peptides, or polynucleotides of the present invention as an active ingredient. Alternatively, the present peptides may be expressed on the surface of any of the foregoing exosomes or cells, such as APCs for the use as pharmaceutical substances or compositions. In addition, the aforementioned CTLs which target any of the peptides of the present invention may also be used as the active ingredient of the present pharmaceutical substances or compositions.

The present pharmaceutical agents, substances or compositions find use as a vaccine. In the present invention, the phrase "vaccine" (also referred to as an immunogenic composition) refers to a substance that has the function to induce anti-tumor immunity upon inoculation into animals.

The pharmaceutical agents, substances or compositions of the present invention can be used to treat and/or prevent cancers, and/or prevention of postoperative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal.

In another embodiment, the present invention also provides the use of an active ingredient in manufacturing a pharmaceutical agents, substance or composition formulated for the treatment and/or prevention of cancers or tumors, said active ingredient selected from among:
(a) a peptide of the present invention;
(b) a nucleic acid encoding such a peptide as disclosed herein in an expressible form;
(c) an APC or an exosome presenting a peptide of the present invention on its surface; and
(d) a cytotoxic T cell of the present invention.

Alternatively, the present invention further provides an active ingredient for use in treating or preventing cancer or tumor, said active ingredient selected from among:
(a) a peptide of the present invention;
(b) a nucleic acid encoding such a peptide as disclosed herein in an expressible form;
(c) an APC or an exosome presenting a peptide of the present invention on its surface; and
(d) a cytotoxic T cell of the present invention.

Alternatively, the present invention further provides a method or process for manufacturing a pharmaceutical agent, composition or substance for the treatment or the prevention of cancer or tumor, wherein the method or process includes the step of formulating a pharmaceutically or physiologically acceptable carrier with an active ingredient selected from among:
(a) a peptide of the present invention;
(b) a nucleic acid encoding such a peptide as disclosed herein in an expressible form;
(c) an APC or an exosome presenting a peptide of the present invention on its surface; and
(d) a cytotoxic T cell of the present invention.

In another embodiment, the present invention also provides a method or process for manufacturing a pharmaceutical agent, composition or substance for the treatment or the prevention of cancer or tumor, wherein the method or process includes the steps of admixing an active ingredient with a pharmaceutically or physiologically acceptable carrier, wherein the active ingredient is selected from among:
(a) a peptide of the present invention;
(b) a nucleic acid encoding such a peptide as disclosed herein in an expressible form;
(c) an APC or an exosome presenting a peptide of the present invention on its surface; and
(d) a cytotoxic T cell of the present invention.

According to the present invention, peptides having an amino acid sequence selected from among SEQ ID NOs: 1 to 40 have been found to be HLA-A2 restricted epitope peptides or the candidates that may induce potent and specific immune response. Therefore, the present pharmaceutical substances or compositions which include any of these peptides with the amino acid sequences of SEQ ID NOs: 1 to 40 are particularly suited for the administration to subjects whose HLA antigen is HLA-A2. The same applies to pharmaceutical substances or compositions which include polynucleotides encoding any of these peptides (i.e., the polynucleotides of the present invention).

Cancers to be treated by the pharmaceutical, substances or compositions of the present invention are not limited and include any cancer in which ECT2 is involved (e.g., is overexpressed), including, but not limited to, bladder cancer, breast cancer, cervical cancer, cholangiocellular carcinoma, CML, colorectal cancer, esophageal cancer, NSCLC, lymphoma, pancreatic cancer, prostate cancer, renal carcinoma and SCLC.

The present pharmaceutical, substances or compositions may contain in addition to the aforementioned active ingredients, other peptides which have the ability to induce CTLs against cancerous cells, other polynucleotides encoding the other peptides, other cells that present the other peptides, or such. Herein, the other peptides that have the ability to induce CTLs against cancerous cells are exemplified by cancer specific antigens (e.g., identified TAAs), but are not limited thereto.

If needed, the pharmaceutical, substances or compositions of the present invention may optionally include other therapeutic substances as an active ingredient, so long as the substance does not inhibit the antitumoral effect of the active ingredient, e.g., any of the present peptides. For example, formulations may include anti-inflammatory substances or compositions, pain killers, chemotherapeutics, and the like. In addition to other therapeutic substances in the medicament itself, the medicaments of the present invention may also be administered sequentially or concurrently with the one or more other pharmacologic substances or compositions. The amounts of medicament and pharmacologic substance or composition depend, for example, on what type of pharmacologic substance(s) or composition(s) is/are used, the disease being treated, and the scheduling and routes of administration.

It should be understood that in addition to the ingredients particularly mentioned herein, the pharmaceutical substances or compositions of the present invention may include other substances or compositions conventional in the art having regard to the type of formulation in question.

In one embodiment of the present invention, the present pharmaceutical substances or compositions may be included in articles of manufacture and kits containing materials useful for treating the pathological conditions of the disease to be treated, e.g., cancer. The article of manufacture may include a container of any of the present pharmaceutical substances or compositions with a label. Suitable containers include bottles, vials, and test tubes. The containers may be formed from a variety of materials, such as glass or plastic. The label on the container should indicate the substance or composition is used for treating or prevention of one or more conditions of the disease. The label may also indicate directions for administration and so on.

In addition to the container described above, a kit including a pharmaceutical substance or composition of the present invention may optionally further include a second container housing a pharmaceutically-acceptable diluent. It may further include other materials desirable from a commercial and user standpoint, including other buffers, diluents, filters, needles, syringes, and package inserts with instructions for use.

The pharmaceutical compositions can, if desired, be presented in a pack or dispenser device which can contain one or more unit dosage forms containing the active ingredient. The pack can, for example, include metal or plastic foil, such as a blister pack. The pack or dispenser device can be accompanied by instructions for administration.

(1) Pharmaceutical Substances or Compositions Containing the Peptides as the Active Ingredient The peptides of the present invention can be administered directly as a pharmaceutical substance or composition, or if necessary, may be formulated by conventional formulation methods. In the latter case, in addition to the peptides of the present invention, carriers, excipients, and such that are ordinarily used for drugs can be included as appropriate without particular limitations. Examples of such carriers are sterilized water, physiological saline, phosphate buffer, culture fluid and such. Furthermore, the pharmaceutical substances or compositions can contain as necessary, stabilizers, suspensions, preservatives, surfactants and such. The pharmaceutical substances or compositions of the present invention can be used for anticancer purposes.

The peptides of the present invention can be prepared in combination, which includes two or more of peptides of the present invention, to induce CTL in vivo. The peptides can be in a cocktail or can be conjugated to each other using standard techniques. For example, the peptides can be chemically linked or expressed as a single fusion polypeptide sequence that may have one or several amino acid(s) as a linker (e.g., Lysine linker: K. S. Kawamura et al. J. Immunol. 2002, 168: 5709-5715). The peptides in the combination can be the same or different. By administering the peptides of the present invention, the peptides are presented in high density by the HLA antigens on APCs, then CTLs that specifically react toward the complex formed between the displayed peptide and the HLA antigen are induced. Alternatively, APCs (e.g., DCs) are removed from subjects and then stimulated by the peptides of the present invention to obtain APCs that present any of the peptides of the present invention on their cell surface. These APCs are readministered to the subjects to induce CTLs in the subjects, and as a result, aggressiveness towards the tumor-associated endothelium can be increased.

The pharmaceutical agent, substances or compositions for the treatment and/or prevention of cancer, which include any of the peptides of the present invention as the active ingredient, can also include an adjuvant so that cellular immunity will be established effectively. Alternatively, the pharmaceutical agent, substance or composition can be administered with other active ingredients or can be administered by formulation into granules. An adjuvant refers to any compound, substance or composition that enhances the immune response against the protein when administered together (or successively) with the protein having immunological activity. An adjuvant that can be applied includes those described in the literature (Clin Microbiol Rev 1994, 7: 277-89). Exemplary adjuvants include aluminum phosphate, aluminum hydroxide, alum, cholera toxin, *salmonella* toxin, Incomplete Freund's adjuvant (IFA), Complete Freund's adjuvant (CFA), ISCOMatrix, GM-CSF, CpG, O/W emulsion, and such, but are not limited thereto.

Furthermore, liposome formulations, granular formulations in which the peptide is bound to few-micrometers diameter beads, and formulations in which a lipid is bound to the peptide may be conveniently used.

In another embodiment of the present invention, the peptides of the present invention may also be administered in the form of a pharmaceutically acceptable salt. Preferable examples of the salts include salts with an alkali metal, salts with a metal, salts with an organic base, salts with an organic acid and salts with an inorganic acid.

In some embodiments, the pharmaceutical substances or compositions of the present invention include a component which primes CTL. Lipids have been identified as substances or compositions capable of priming CTL in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of CTL responses, *E. coli* lipoproteins, such as tripalmitoyl-S-glycerylcysteinyl-seryl-serine (P3CSS) can be used to prime CTL when covalently attached to an appropriate peptide (see, e.g., Deres et al., Nature 1989, 342: 561-4).

The method of administration can be oral, intradermal, subcutaneous, intravenous injection, or such, and systemic administration or local administration to the vicinity of the targeted sites. The administration can be performed by single administration or boosted by multiple administrations. The dose of the peptides of the present invention can be adjusted appropriately according to the disease to be treated, age of the patient, weight, method of administration, and such, and is ordinarily 0.001 mg to 1,000 mg, for example, 0.01 mg to 100 mg, for example, 0.1 mg to 10 mg, and can be administered once in a few days to few months. One skilled in the art can appropriately select a suitable dose.

(2) Pharmaceutical Substances or Compositions Containing Polynucleotides as Active Ingredient The pharmaceutical agent, substances or compositions of the present invention can also include nucleic acids encoding the peptide(s) disclosed herein in an expressible form. Herein, the phrase "in an expressible form" means that the polynucleotide, when introduced into a cell, will be expressed in vivo as a polypeptide that induces anti-tumor immunity. In an exemplified embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors. See also, e.g., Wolff et al., Science 1990, 247: 1465-8; U.S. Pat. Nos. 5,580,859; 5,589,466; 5,804,566; 5,739,118; 5,736,524; 5,679,647; and WO 98/04720). Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the present invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization, e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a patient can be either direct, in which case the patient is directly exposed to a polynucleotide-carrying vector, or indirect, in which case, cells are first transformed with the polynucleotide of interest in vitro, then the cells are transplanted into the patient. Theses two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology that are applicable to the present invention are described by Ausubel et al., in Current Protocols in Molecular Biology, John Wiley & Sons, NY, 1993; and by Krieger, in Gene Transfer and Expression, A Laboratory Manual, Stockton Press, NY, 1990.

The method of administration can be oral, intradermal, subcutaneous, intravenous injection, or such, and systemic administration or local administration to the vicinity of the targeted sites finds use. The administration can be performed by single administration or boosted by multiple administrations. The dose of the polynucleotide in the suitable carrier or cells transformed with the polynucleotide encoding the peptides of the present invention can be adjusted appropriately according to the disease to be treated, age of the patient, weight, method of administration, and such, and is ordinarily 0.001 mg to 1,000 mg, for example, 0.01 mg to 100 mg, for example, 0.1 mg to 10 mg, and can be administered once every a few days to once every few months. One skilled in the art can appropriately select the suitable dose.

X. METHODS USING THE PEPTIDES, EXOSOMES, APCS AND CTLS

The peptides and polynucleotides of the present invention can be used for preparing or inducing APCs and CTLs. The exosomes and APCs of the present invention can be also used for inducing CTLs. The peptides, polynucleotides, exosomes and APCs can be used in combination with any other compounds so long as the additional compounds do not inhibit CTL inducibility. Thus, any of the aforementioned pharmaceutical substances or compositions of the present invention can be used for inducing CTLs. In addition thereto, those including the peptides and polynucleotides can be also be used for inducing APCs as explained below.

(1) Method of Inducing Antigen-Presenting Cells (APCs)

The present invention provides methods of inducing APCs with high CTL inducibility using the peptides or polynucleotides of the present invention.

The methods of the present invention include the step of contacting APCs with the peptides of the present invention in vitro, ex vivo or in vivo. For example, the method contacting APCs with the peptides ex vivo can include steps of:

a: collecting APCs from a subject, and b: contacting the APCs of step a with the peptide.

The APCs are not limited to a particular kind of cells and include DCs, Langerhans cells, macrophages, B cells, and activated T cells, which are known to present proteinaceous antigens on their cell surface so as to be recognized by lymphocytes. Preferably, DCs can be used since they have the strongest CTL inducibility among APCs. Any peptides of the present invention can be used by themselves or with other peptides of the present invention.

On the other hands, when the peptides of the present invention are administered to a subject, the APCs are contacted with the peptides in vivo, consequently, the APCs with high CTL inducibility are induced in the body of the subject. Thus, the present invention includes administering the peptides of the present invention to a subject. Similarly, when the polynucleotides of the present invention are administered to a subject in an expressible form, the peptides of the present invention are expressed and contacted with APCs in vivo, consequently, the APCs with high CTL inducibility are induced in the body of the subject. Thus, the present invention may also include administering the polynucleotides of the present invention to a subject. The phrase "expressible form" is described above in section "IX. Pharmaceutical substances and compositions, (2) Pharmaceutical substances or compositions containing polynucleotides as the active ingredient".

Furthermore, the present invention may include introducing the polynucleotide of the present invention into an APCs to induce APCs with CTL inducibility. For example, the method can include steps of:

a: collecting APCs from a subject, and b: introducing a polynucleotide encoding peptide of the present invention.

Step b can be performed as described above in section "VI. Antigen-presenting cells".

Alternatively, the present invention provides a method for preparing an antigen-presenting cell (APC) which specifically induces CTL activity against ECT2, wherein the method can include one of the following steps:

(a) contacting an APC with a peptide of the present invention in vitro, ex vivo or in vivo; and (b) introducing a polynucleotide encoding a peptide of the present invention into an APC.

(2) Method of Inducing CTLs

The present invention also provides methods for inducing CTLs using the peptides, polynucleotides, exosomes or APCs of the present invention.

The present invention also provides methods for inducing CTLs using a polynucleotide encoding a polypeptide that is capable of forming a T cell receptor (TCR) subunit recognizing a complex of the peptides of the present invention and HLA antigens. Preferably, the methods for inducing CTLs may include at least one step selected from among:

a) contacting a CD8 positive T cell with an antigen-presenting cell and/or an exosome that presents on its surface a complex of an HLA antigen and a peptide of the preset invention; and b) introducing a polynucleotide encoding a polypeptide that is capable of forming a TCR subunit recognizing a complex of a peptide of the present invention and an HLA antigen into a CD8 positive cell.

When the peptides, the polynucleotides, APCs, or exosomes of the present invention are administered to a subject, CTLs are induced in the body of the subject, and the strength of the immune response targeting the cancer cells is enhanced. Thus, the methods of the present invention includes the step of administering the peptides, the polynucleotides, the APCs or exosomes of the present invention to a subject.

Alternatively, CTLs can be also induced by using them ex vivo, and after inducing CTL, the activated CTLs can be returned to the subject. For example, the method can include steps of:

a: collecting APCs from a subject;

b: contacting with the APCs of step a, with the peptide; and c: co-culturing the APCs of step b with CD8 positive cells.

The APCs to be co-cultured with the CD8 positive cells in above step c can also be prepared by transferring a gene that includes a polynucleotide of the present invention into APCs as described above in section "VI. Antigen-presenting cells" though the present invention is not limited thereto, and encompasses any APCs that effectively present on the surface a complex of an HLA antigen and a peptide of the present invention.

Instead of such APCs, the exosomes that presents on its surface a complex of an HLA antigen and the peptide of the present invention can be also used. Namely, the present invention can include the step of co-culturing exosomes presenting on its surface a complex of an HLA antigen and the peptide of the present invention. Such exosomes can be prepared by the methods described above in section "V. Exosomes".

Furthermore, CTL can be induced by introducing a gene that includes a polynucleotide encoding the TCR subunit binding to the peptide of the present invention into CD8 positive cells. Such transduction can be performed as described above in section "VIII. T cell receptor (TCR)".

In addition, the present invention provides a method or process for manufacturing a pharmaceutical substance or composition inducing CTLs, wherein the method includes the step of admixing or formulating the peptide of the present invention with a pharmaceutically acceptable carrier.

(3) Method of Inducing Immune Response

Moreover, the present invention provides methods of inducing an immune response against diseases related to ECT2. Suitable diseases may include cancer, examples of which include, but are not limited to, bladder cancer, breast cancer, cervical cancer, cholangiocellular carcinoma, CML, colorectal cancer, esophageal cancer, NSCLC, lymphoma, pancreatic cancer, prostate cancer, renal carcinoma and SCLC.

The methods of the present invention may include the step of administering substance(s) or composition(s) containing any of the peptides of the present invention or polynucleotides encoding them. The present inventive method may also contemplate the administration of exosomes or APCs presenting any of the peptides of the present invention. For details, see the item of "IX. Pharmaceutical substances or compositions", particularly the part describing the use of the pharmaceutical substances or compositions of the present invention as vaccines. In addition, the exosomes and APCs that can be employed for the present methods for inducing immune response are described in detail under the items of "V. Exosomes", "VI. Antigen-presenting cells (APCs)", and (1) and (2) of "X. Methods using the peptides, exosomes, APCs and CTLs", supra.

The present invention also provides a method or process for manufacturing a pharmaceutical substance or composition inducing immune response, wherein the method may include the step of admixing or formulating the peptide of the present invention with a pharmaceutically acceptable carrier.

Alternatively, the method of the present invention may include the step of administrating a vaccine or a pharmaceutical composition of the present invention that contains:

(a) a peptide of the present invention;

(b) a nucleic acid encoding such a peptide as disclosed herein in an expressible form;

(c) an APC or an exosome presenting a peptide of the present invention on its surface; or (d) a cytotoxic T cell of the present invention.

In the context of the present invention, a cancer overexpressing ECT2 can be treated with these active ingredients. Examples of such cancers include, but are not limited to, bladder cancer, breast cancer, cervical cancer, cholangiocellular carcinoma, CML, colorectal cancer, esophageal cancer, NSCLC, lymphoma, pancreatic cancer, prostate cancer, renal carcinoma and SCLC. Accordingly, prior to the administration of the vaccines or pharmaceutical compositions including the active ingredients, it is preferable to confirm whether the expression level of ECT2 in the cells or tissues to be treated is enhanced compared with normal cells of the same organ. Thus, in one embodiment, the present invention provides a method for treating cancer (over)expressing ECT2, which method may include the steps of:

i) determining the expression level of ECT2 in cells or tissue(s) obtained from a subject with the cancer to be treated;

ii) comparing the expression level of ECT2 with normal control; and iii) administering at least one component selected from among (a) to (d) described above to a subject with cancer overexpressing ECT2 compared with normal control.

Alternatively, the present invention also provides a vaccine or pharmaceutical composition that includes at least one component selected from among (a) to (d) described above, for use in administrating to a subject having cancer overexpressing ECT2. In other words, the present invention further provides a method for identifying a subject to be treated with the ECT2 polypeptide of the present invention, such method including the step of determining an expression level of ECT2 in subject-derived cells or tissue(s), wherein an increase of the level compared to a normal control level of the gene indicates that the subject may have cancer which may be treated with the ECT2 polypeptide of the present invention. The methods of treating cancer of the present invention are described in more detail below.

Any subject-derived cell or tissue can be used for the determination of ECT2 expression so long as it includes the objective transcription or translation product of ECT2. Examples of suitable samples include, but are not limited to, bodily tissues and fluids, such as blood, sputum and urine. Preferably, the subject-derived cell or tissue sample contains a cell population including an epithelial cell, more preferably a cancerous epithelial cell or an epithelial cell derived from tissue suspected to be cancerous. Further, if necessary, the cell may be purified from the obtained bodily tissues and fluids, and then used as the subjected-derived sample.

A subject to be treated by the present method is preferably a mammal. Exemplary mammals include, but are not limited to, e.g., human, non-human primate, mouse, rat, dog, cat, horse, and cow.

According to the present invention, the expression level of ECT2 in cells or tissues obtained from a subject may be determined. The expression level can be determined at the transcription (nucleic acid) product level, using methods known in the art. For example, the mRNA of ECT2 may be quantified using probes by hybridization methods (e.g., Northern hybridization). The detection may be carried out on a chip, an array or as such. The use of an array may be preferable for detecting the expression level of ECT2. Those skilled in the art can prepare such probes utilizing the sequence information of ECT2. For example, the cDNA of ECT2 may be used as the probes. If necessary, the probes may be labeled with a suitable label, such as dyes, fluorescent substances and isotopes, and the expression level of the gene may be detected as the intensity of the hybridized labels.

Furthermore, the transcription product of ECT2 (e.g., SEQ ID NO: 42) may be quantified using primers by amplification-based detection methods (e.g., RT-PCR). Such primers may be prepared based on the available sequence information of the gene.

Specifically, a probe or primer used for the present method hybridizes under stringent, moderately stringent, or low stringent conditions to the mRNA of ECT2. As used herein, the phrase "stringent (hybridization) conditions" refers to conditions under which a probe or primer will hybridize to its target sequence, but not to other sequences. Stringent conditions are sequence-dependent and will be different under different circumstances. Specific hybridization of longer sequences is observed at higher temperatures than shorter sequences. Generally, the temperature of a stringent condition is selected to be about 5 degrees C. lower than the thermal melting point (Tm) for a specific sequence at a defined ionic strength and pH. The Tm is the temperature (under a defined ionic strength, pH and nucleic acid concentration) at which 50% of the probes complementary to their target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degrees C. for short probes or primers (e.g., 10 to 50 nucleotides) and at least about 60 degrees C. for longer probes or primers. Stringent conditions may also be achieved with the addition of destabilizing substances, such as formamide.

A probe or primer of the present invention is typically a substantially purified oligonucleotide. The oligonucleotide typically includes a region of nucleotide sequence that hybridizes under stringent conditions to at least about 2000, 1000, 500, 400, 350, 300, 250, 200, 150, 100, 50, or 25, consecutive sense strand nucleotide sequence of a nucleic acid including an ECT2 sequence, or an anti sense strand nucleotide sequence of a nucleic acid comprising a ECT2 sequence, or of a naturally occurring mutant of these sequences. In particular, for example, in a preferred embodiment, an oligonucleotide having 5-50 in length can be used as a primer for amplifying the genes, to be detected. More preferably, mRNA or cDNA of a ECT2 gene can be detected with oligonucleotide probe or primer of a specific size, generally 15-30 b in length.

In preferred embodiments, length of the oligonucleotide probe or primer can be selected from 15-25. Assay procedures, devices, or reagents for the detection of gene by using such oligonucleotide probe or primer are well known (e.g. oligonucleotide microarray or PCR). In these assays, probes or primers can also include tag or linker sequences. Further, probes or primers can be modified with detectable label or affinity ligand to be captured. Alternatively, in hybridization based detection procedures, a polynucleotide having a few hundreds (e.g., about 100-200) bases to a few kilo (e.g., about 1000-2000) bases in length can also be used for a probe (e.g., northern blotting assay or cDNA microarray analysis).

Alternatively, the translation product may be detected for the diagnosis of the present invention. For example, the quantity of ECT2 protein (SEQ ID NO: 42) or the immunologically fragment thereof may be determined. Methods for determining the quantity of the protein as the translation product include immunoassay methods that use an antibody specifically recognizing the protein. The antibody may be monoclonal or polyclonal. Furthermore, any fragment or modification (e.g., chimeric antibody, scFv, Fab, F(ab')$_2$, Fv, etc.) of the antibody may be used for the detection, so long as the fragment or modified antibody retains the binding ability to the ECT2 protein. Such antibodies against the peptides of the present invention and the fragments thereof are also provided by the present invention. Methods to prepare these kinds of antibodies for the detection of proteins are well known in the art, and any method may be employed in the present invention to prepare such antibodies and equivalents thereof.

As another method to detect the expression level of ECT2 gene based on its translation product, the intensity of staining may be measured via immunohistochemical analysis using an antibody against the ECT2 protein. Namely, in this measurement, strong staining indicates increased presence/level of the protein and, at the same time, high expression level of ECT2 gene.

The expression level of a target gene, e.g., the ECT2 gene, in cancer cells can be determined to be increased if the level increases from the control level (e.g., the level in normal cells)

of the target gene by, for example, 10%, 25%, or 50%; or increases to more than 1.1 fold, more than 1.5 fold, more than 2.0 fold, more than 5.0 fold, more than 10.0 fold, or more.

The control level may be determined at the same time as the cancer cells using a sample(s) previously collected and stored from a subject(s) whose disease state(s) (cancerous or non-cancerous) is/are known. In addition, normal cells obtained from non-cancerous regions of an organ that has the cancer to be treated may be used as normal control. Alternatively, the control level may be determined by a statistical method based on the results obtained by analyzing previously determined expression level(s) of ECT2 gene in samples from subjects whose disease states are known. Furthermore, the control level can be derived from a database of expression patterns from previously tested cells. Moreover, according to an aspect of the present invention, the expression level of ECT2 gene in a biological sample may be compared to multiple control levels, determined from multiple reference samples. It is preferred to use a control level determined from a reference sample derived from a tissue type similar to that of the subject-derived biological sample. Moreover, it is preferred to use the standard value of the expression levels of ECT2 gene in a population with a known disease state. The standard value may be obtained by any method known in the art. For example, a range of mean+/−2 S.D. or mean+/−3 S.D. may be used as the standard value.

In the context of the present invention, a control level determined from a biological sample that is known to be non-cancerous is referred to as a "normal control level". On the other hand, if the control level is determined from a cancerous biological sample, it is referred to as a "cancerous control level". Difference between a sample expression level and a control level can be normalized to the expression level of control nucleic acids, e.g., housekeeping genes, whose expression levels are known not to differ depending on the cancerous or non-cancerous state of the cell. Exemplary control genes include, but are not limited to, beta-actin, glyceraldehyde 3 phosphate dehydrogenase, and ribosomal protein P1.

When the expression level of ECT2 gene is increased as compared to the normal control level, or is similar/equivalent to the cancerous control level, the subject may be diagnosed with cancer to be treated.

The present invention also provides a method of (i) diagnosing whether a subject suspected to have cancer to be treated, and/or (ii) selecting a subject for cancer treatment, which method may include the steps of:

a) determining the expression level of ECT2 in cells or tissue(s) obtained from a subject who is suspected to have the cancer to be treated;

b) comparing the expression level of ECT2 with a normal control level;

c) diagnosing the subject as having the cancer to be treated, if the expression level of ECT2 is increased as compared to the normal control level; and d) selecting the subject for cancer treatment, if the subject is diagnosed as having the cancer to be treated, in step c).

Alternatively, such a method may include the steps of:

a) determining the expression level of ECT2 in cells or tissue(s) obtained from a subject who is suspected to have the cancer to be treated;

b) comparing the expression level of ECT2 with a cancerous control level;

c) diagnosing the subject as having the cancer to be treated, if the expression level of ECT2 is similar or equivalent to the cancerous control level; and d) selecting the subject for cancer treatment, if the subject is diagnosed as having the cancer to be treated, in step c).

The present invention also provides a diagnostic kit for diagnosing or determining a subject who is or is suspected to be suffering from cancer that can be treated with the ECT2 polypeptide of the present invention, which may also find use in assessing and/or monitoring the efficacy or applicability of a cancer immunotherapy. Preferably, the cancer includes, but is not limited to, bladder cancer, breast cancer, cervical cancer, cholangiocellular carcinoma, CML, colorectal cancer, esophageal cancer, NSCLC, lymphoma, pancreatic cancer, prostate cancer, renal carcinoma and SCLC. More particularly, the kit preferably may include at least one reagent for detecting the expression of the ECT2 gene in a subject-derived cell, which reagent may be selected from the group of:

(a) a reagent for detecting mRNA of the ECT2 gene;

(b) a reagent for detecting the ECT2 protein or the immunologically fragment thereof; and (c) a reagent for detecting the biological activity of the ECT2 protein.

Examples of reagents suitable for the detection of mRNA of the ECT2 gene may include nucleic acids that specifically bind to or identify the ECT2 mRNA, such as oligonucleotides that have a complementary sequence to a portion of the ECT2 mRNA. These kinds of oligonucleotides are exemplified by primers and probes that are specific to the ECT2 mRNA. These kinds of oligonucleotides may be prepared based on methods well known in the art. If needed, the reagent for detecting the ECT2 mRNA may be immobilized on a solid matrix. Moreover, more than one reagent for detecting the ECT2 mRNA may be included in the kit.

On the other hand, examples of reagents suitable for the detection of the ECT2 protein or the immunologically fragment thereof may include antibodies to the ECT2 protein or the immunologically fragment thereof. The antibody may be monoclonal or polyclonal. Furthermore, any fragment or modification (e.g., chimeric antibody, scFv, Fab, F(ab')$_2$, Fv, etc.) of the antibody may be used as the reagent, so long as the fragment or modified antibody retains the binding ability to the ECT2 protein or the immunologically fragment thereof. Methods to prepare these kinds of antibodies for the detection of proteins are well known in the art, and any method may be employed in the present invention to prepare such antibodies and equivalents thereof. Furthermore, the antibody may be labeled with signal generating molecules via direct linkage or an indirect labeling technique. Labels and methods for labeling antibodies and detecting the binding of the antibodies to their targets are well known in the art, and any labels and methods may be employed for the present invention. Moreover, more than one reagent for detecting the ECT2 protein may be included in the kit.

The kit may contain more than one of the aforementioned reagents. The kit can further include a solid matrix and reagent for binding a probe against an ECT2 gene or antibody against an ECT2 peptide, a medium and container for culturing cells, positive and negative control reagents, and a secondary antibody for detecting an antibody against an ECT2 peptide. For example, tissue samples obtained from subjects without cancer or suffering from cancer, may serve as useful control reagents. A kit of the present invention may further include other materials desirable from a commercial and user standpoint, including buffers, diluents, filters, needles, syringes, and package inserts (e.g., written, tape, CD-ROM, etc.) with instructions for use. These reagents and such may be retained in a container with a label. Suitable containers may include bottles, vials, and test tubes. The containers may be formed from a variety of materials, such as glass or plastic.

In an embodiment of the present invention, when the reagent is a probe against the ECT2 mRNA, the reagent may be immobilized on a solid matrix, such as a porous strip, to form at least one detection site. The measurement or detection region of the porous strip may include a plurality of sites, each containing a nucleic acid (probe). A test strip may also contain sites for negative and/or positive controls. Alternatively, control sites may be located on a strip separated from the test strip. Optionally, the different detection sites may contain different amounts of immobilized nucleic acids, i.e., a higher amount in the first detection site and lesser amounts in subsequent sites. Upon the addition of a test sample, the number of sites displaying a detectable signal provides a quantitative indication of the amount of ECT2 mRNA present in the sample. The detection sites may be configured in any suitably detectable shape and are typically in the shape of a bar or dot spanning the width of a test strip.

The kit of the present invention may further include a positive control sample or ECT2 standard sample. The positive control sample of the present invention may be prepared by collecting ECT2 positive samples and then assaying their ECT2 levels. Alternatively, a purified ECT2 protein or polynucleotide may be added to cells that do not express ECT2 to form the positive sample or the ECT2 standard sample. In the present invention, purified ECT2 may be a recombinant protein. The ECT2 level of the positive control sample is, for example, more than the cut off value.

In one embodiment, the present invention further provides a diagnostic kit including, a protein or a partial protein thereof capable of specifically recognizing the antibody of the present invention or the fragment thereof.

Examples of partial peptides of the present invention include polypeptides composed of at least 8, preferably 15, and more preferably 20 contiguous amino acids in the amino acid sequence of a protein of the present invention. Cancer can be diagnosed by detecting an antibody in a sample (e.g., blood, tissue) using a protein or a peptide (polypeptide) of the present invention. The method for preparing the protein of the present invention and peptides are as described above.

The methods for diagnosing cancer of the present invention can be performed by determining the difference between the amount of anti-ECT2 antibody and that in the corresponding control sample as describe above. The subject is suspected to be suffering from cancer, if cells or tissues of the subject contain antibodies against the expression products (ECT2) of the gene and the quantity of the anti-ECT2 antibody is determined to be more than the cut off value in level compared to that in normal control.

In another embodiment, a diagnostic kit of the present invention may include the peptide of the present invention and an HLA molecule binding thereto. The method for detecting antigen specific CTLs using antigenic peptides and HLA molecules has already been established (for example, Altman J D et al., Science. 1996, 274(5284): 94-6). Thus, the complex of the peptide of the present invention and the HLA molecule can be applied to the detection method to detect tumor antigen specific CTLs, thereby enabling earlier detection, recurrence and/or metastasis of cancer. Further, it can be employed for the selection of subjects applicable with the pharmaceuticals including the peptide of the present invention as an active ingredient, or the assessment of the treatment effect of the pharmaceuticals.

Particularly, according to the known method (see, for example, Altman J D et al., Science. 1996, 274(5284): 94-6), the oligomer complex, such as tetramer, of the radiolabeled HLA molecule and the peptide of the present invention can be prepared. With using the complex, the diagnosis can be done, for example, by quantifying the antigen-peptide specific CTLs in the peripheral blood lymphocytes derived from the subject suspected to be suffering from cancer.

The present invention further provides a method or diagnostic agents for evaluating immunological response of subject by using peptide epitopes as described herein. In one embodiment of the invention, HLA-A02 restricted peptides as described herein may be used as reagents for evaluating or predicting an immune response of a subject. The immune response to be evaluated may be induced by contacting an immunogen with immunocompetent cells in vitro or in vivo. In some embodiments, any substances or compositions that may result in the production of antigen specific CTLs that recognize and bind to the peptide epitope(s) may be employed as the reagent. The peptide reagents may need not to be used as the immunogen. Assay systems that are used for such an analysis include relatively recent technical developments such as tetramers, staining for intracellular lymphokines and interferon release assays, or ELISPOT assays. In preferred embodiments, the immunocompetent cells for evaluating an immunological response, may be selected from among peripheral blood, peripheral blood lymphocyte (PBL), and peripheral blood mononuclear cell (PBMC). Methods for collecting or isolating such immunocompetent cells are well known in the arts. In an alternate preferred embodiment, the immunocompetent cells to be contacted with peptide reagent include antigen presenting cells such as dendritic cells.

For example, peptides of the present invention may be used in tetramer staining assays to assess peripheral blood mononuclear cells for the presence of antigen-specific CTLs following exposure to a tumor cell antigen or an immunogen. The HLA tetrameric complex may be used to directly visualize antigen specific CTLs (see, e.g., Ogg et al., Science 279: 2103-2106, 1998; and Altman et al, Science 174: 94-96, 1996) and determine the frequency of the antigen-specific CTL population in a sample of peripheral blood mononuclear cells. A tetramer reagent using a peptide of the invention may be generated as described below.

A peptide that binds to an HLA molecule is refolded in the presence of the corresponding HLA heavy chain and beta 2-microglobulin to generate a trimolecular complex. In the complex, carboxyl terminal of the heavy chain is biotinylated at a site that was previously engineered into the protein. Then, streptavidin is added to the complex to form tetramer composed of the trimolecular complex and streptavidin. By means of fluorescently labeled streptavidin, the tetramer can be used to stain antigen specific cells. The cells can then be identified, for example, by flow cytometry. Such an analysis may be used for diagnostic or prognostic purposes. Cells identified by the procedure can also be used for therapeutic purposes.

The present invention also provides reagents to evaluate immune recall responses (see, e.g., Bertoni et al, J. Clin. Invest. 100: 503-513, 1997 and Penna et al., J. Exp. Med. 174: 1565-1570, 1991) including peptides of the present invention. For example, patient PBMC samples from individuals with cancer to be treated can be analyzed for the presence of antigen-specific CTLs using specific peptides. A blood sample containing mononuclear cells can be evaluated by cultivating the PBMCs and stimulating the cells with a peptide of the invention. After an appropriate cultivation period, the expanded cell population can be analyzed, for example, for CTL activity.

The peptides may also be used as reagents to evaluate the efficacy of a vaccine. PBMCs obtained from a patient vaccinated with an immunogen may be analyzed using, for example, either of the methods described above. The patient is HLA typed, and peptide epitope reagents that recognize the allele-specific molecules present in the patient are selected for the analysis. The immunogenicity of the vaccine may be indicated by the presence of epitope-specific CTLs in the PBMC sample. The peptides of the invention may also be used to make antibodies, using techniques well known in the art (see, e.g., CURRENT PROTOCOLS IN IMMUNOLOGY, Wiley/Greene, NY; and Antibodies A Laboratory Manual, Harlow and Lane, Cold Spring Harbor Laboratory Press, 1989), which may find use as reagents to diagnose, detect or monitor cancer. Such antibodies may include those that recognize a peptide in the context of an HLA molecule, i.e., antibodies that bind to a peptide-MHC complex.

The peptides and compositions of the present invention have a number of additional uses, some of which are described herein. For instance, the present invention provides a method for diagnosing or detecting a disorder characterized by expression of a ECT2 immunogenic polypeptide. These methods involve determining expression of a ECT2 HLA binding peptide, or a complex of a ECT2 HLA binding peptide and an HLA class I molecule in a biological sample. The expression of a peptide or complex of peptide and HLA class I molecule can be determined or detected by assaying with a binding partner for the peptide or complex. In a preferred embodiment, a binding partner for the peptide or complex may be an antibody recognizes and specifically bind to the peptide. The expression of ECT2 in a biological sample, such as a tumor biopsy, can also be tested by standard PCR amplification protocols using ECT2 primers. An example of tumor expression is presented herein and further disclosure of exemplary conditions and primers for ECT2 amplification can be found in WO2003/27322, the contents of which are incorporated by reference herein.

Preferably, the diagnostic methods involve contacting a biological sample isolated from a subject with an agent specific for the ECT2 HLA binding peptide to detect the presence of the ECT2 HLA binding peptide in the biological sample. As used herein, "contacting" means placing the biological sample in sufficient proximity to the agent and under the appropriate conditions of, e.g., concentration, temperature, time, ionic strength, to allow the specific interaction between the agent and ECT2 HLA binding peptide that are present in the biological sample. In general, the conditions for contacting the agent with the biological sample are conditions known by those of ordinary skill in the art to facilitate a specific interaction between a molecule and its cognate (e.g., a protein and its receptor cognate, an antibody and its protein antigen cognate, a nucleic acid and its complementary sequence cognate) in a biological sample. Exemplary conditions for facilitating a specific interaction between a molecule and its cognate are described in U.S. Pat. No. 5,108,921, issued to Low et al., the contents of which are incorporated by reference herein.

The diagnostic method of the present invention can be performed in either or both of in vivo and in vitro. Accordingly, biological sample can be located in vivo or in vitro in the present invention. For example, the biological sample can be a tissue in vivo and the agent specific for the ECT2 immunogenic polypeptide can be used to detect the presence of such molecules in the tissue. Alternatively, the biological sample can be collected or isolated in vitro (e.g., a blood sample, tumor biopsy, tissue extract). In a particularly preferred embodiment, the biological sample can be a cell-containing sample, more preferably a sample containing tumor cells collected from a subject to be diagnosed or treated.

Alternatively, the diagnosis can be done, by a method which allows direct quantification of antigen-specific T cells by staining with Fluorescein-labeled HLA multimeric complexes (e.g., Altman, J. D. et al., 1996, Science 274: 94; Altman, J. D. et al., 1993, Proc. Natl. Acad. Sci. USA 90: 10330). Staining for intracellular lymphokines, and interferon-gamma release assays or ELISPOT assays also has been provided. Multimer staining, intracellular lymphokine staining and ELISPOT assays all appear to be at least 10-fold more sensitive than more conventional assays (Murali-Krishna, K. et al., 1998, Immunity 8: 177; Lalvani, A. et al., 1997, J. Exp. Med. 186: 859; Dunbar, P. R. et al., 1998, Curr. Biol. 8: 413). Pentamers (e.g., US 2004-209295A), dextramers (e.g., WO 02/072631), and streptamers (e.g., Nature medicine 6. 631-637 (2002)) may also be used.

Accordingly, in some embodiments, the present invention provides a method for diagnosing or evaluating an immunological response of a subject administered at least one of the ECT2 peptides of the present invention, the method including the steps of:

(a) contacting an immunogen with immunocompetent cells under the condition suitable of induction of CTL specific to the immunogen;

(b) detecting or determining induction level of the CTL induced in step (a); and (c) correlating the immunological response of the subject with the CTL induction level.

In the context of the present invention, the immunogen is at least one of (a) an ECT2 peptide selected from among SEQ ID NOs: 1 to 40 and (b) peptides having such amino acid sequences in which such amino acid sequences have been modified with 1, 2 or more amino acid substitution(s). In the meantime, conditions suitable of induction of immunogen specific CTL are well known in the art. For example, immunocompetent cells may be cultured in vitro under the presence of immunogen(s) to induce immunogen specific CTL. In order to induce immunogen specific CTLs, any stimulating factors may be added to the cell culture. For example, IL-2 is preferable stimulating factors for the CTL induction.

In some embodiments, the step of monitoring or evaluating immunological response of a subject to be treated with peptide cancer therapy may be performed before, during and/or after the treatment. In general, during a protocol of cancer therapy, immunogenic peptides are administered repeatedly to a subject to be treated. For example, immunogenic peptides may be administered every week for 3-10 weeks. Accordingly, the immunological response of the subject can be evaluated or monitored during the cancer therapy protocol. Alternatively, the step of evaluation or monitoring of immunological response to the cancer therapy may at the completion of the therapy protocol.

According to the present invention, enhanced induction of immunogen specific CTL as compared with a control indicates that the subject to be evaluated or diagnosed immunologically responded to the immunogen(s) that has/have been administered. Suitable controls for evaluating the immunological response may include, for example, a CTL induction level when the immunocompetent cells are contacted with no peptide, or control peptide(s) having amino acid sequences other than any ECT2 peptides. (e.g. random amino acid sequence). In a preferred embodiment, the immunological response of the subject is evaluated in a sequence specific manner, by comparison with an immunological response between each immunogen administered to the subject. In particular, even when a mixture of some kinds of ECT2 peptides is administered to the subject, immunological response might vary depending on the peptides. In that case, by comparison of the immunological response between each peptide, peptides to which the subject show higher response can be identified.

XI. ANTIBODIES

The present invention further provides antibodies that bind to the peptides of the present invention. Preferred antibodies specifically bind to the peptide of the present invention and will not bind (or will bind weakly) to non-peptide of the present invention. Alternatively, antibodies bind to the peptide of the invention as well as the homologs thereof. Antibodies against the peptide of the invention can find use in cancer diagnostic and prognostic assays, and imaging methodologies. Similarly, such antibodies can find use in the treatment, diagnosis, and/or prognosis of other cancers, to the extent ECT2 is also expressed or overexpressed in cancer patient. Moreover, intracellularly expressed antibodies (e.g., single chain antibodies) may therapeutically find use in treating cancers in which the expression of ECT2 is involved, s examples of which include, but are not limited to, bladder cancer, breast cancer, cervical cancer, cholangiocellular carcinoma, CML, colorectal cancer, esophageal cancer, NSCLC, lymphoma, pancreatic cancer, prostate cancer, renal carcinoma and SCLC.

The present invention also provides various immunological assay for the detection and/or quantification of ECT2 protein (SEQ ID NO: 42) or fragments thereof including polypeptide having an amino acid selected from among SEQ ID NOs: 1 to 40. Such assays may include one or more anti-ECT2 antibodies capable of recognizing and binding a ECT2 protein or fragments thereof, as appropriate. In the present invention, anti-ECT2 antibodies binding to ECT2 polypeptide preferably recognize a polypeptide having an amino acid sequence selected from among SEQ ID NOs: 1 to 40. A binding specificity of antibody can be confirmed with inhibition test. That is, when the binding between an antibody to be analyzed and full-length of ECT2 polypeptide is inhibited under presence of any fragment polypeptides having an amino acid sequence selected from among SEQ ID NOs: 1 to 40, the antibody specifically binds to the fragment. In the context of the present invention, such immunological assays are performed within various immunological assay formats well known in the art, including but not limited to, various types of radioimmunoassays, immuno-chromatograph technique, enzyme-linked immunosorbent assays (ELISA), enzyme-linked immunofluorescent assays (ELIFA), and the like.

Related immunological but non-antibody assays of the invention may also include T cell immunogenicity assays (inhibitory or stimulatory) as well as MHC binding assays. In addition, immunological imaging methods capable of detecting cancers expressing ECT2 are also provided by the invention, including, but not limited to, radioscintigraphic imaging methods using labeled antibodies of the present invention. Such assays can clinically find use in the detection, monitoring, and prognosis of ECT2 expressing cancers including, but not limited to, bladder cancer, breast cancer, cervical cancer, cholangiocellular carcinoma, CML, colorectal cancer, esophageal cancer, NSCLC, lymphoma, pancreatic cancer, prostate cancer, renal carcinoma and SCLC.

The present invention also provides an antibody that binds to the peptide of the invention. The antibody of the invention can be used in any form, such as monoclonal or polyclonal antibodies, and include antiserum obtained by immunizing an animal such as a rabbit with the peptide of the invention, all classes of polyclonal and monoclonal antibodies, human antibodies and humanized antibodies produced by genetic recombination.

A peptide of the invention used as an antigen to obtain an antibody may be derived from any animal species, but preferably is derived from a mammal such as a human, mouse, or rat, more preferably from a human. A human-derived peptide may be obtained from the nucleotide or amino acid sequences disclosed herein.

According to the present invention, the peptide to be used as an immunization antigen may be a complete protein or a partial peptide of the protein. A partial peptide may include, for example, the amino (N)-terminal or carboxy (C)-terminal fragment of a peptide of the present invention.

Herein, an antibody is defined as a protein that reacts with either the full length or a fragment of a ECT2 peptide. In a preferred embodiment, antibody of the present invention can recognize fragment peptides of ECT2 having an amino acid sequence selected from among SEQ ID NOs: 1 to 40. Methods for synthesizing oligopeptide are well known in the arts. After the synthesis, peptides may be optionally purified prior to use as immunogen. In the present invention, the oligopeptide (e.g., 9- or 10mer) may be conjugated or linked with carriers to enhance the immunogenicity. Keyhole-limpet hemocyanin (KLH) is well known as the carrier. Method for conjugating KLH and peptide are also well known in the arts.

Alternatively, a gene encoding a peptide of the invention or fragment thereof may be inserted into a known expression vector, which is then used to transform a host cell as described herein. The desired peptide or fragment thereof may be recovered from the outside or inside of host cells by any standard method, and may subsequently be used as an antigen. Alternatively, whole cells expressing the peptide or their lysates or a chemically synthesized peptide may be used as the antigen.

Any mammalian animal may be immunized with the antigen, but preferably the compatibility with parental cells used for cell fusion is taken into account. In general, animals of Rodentia, Lagomorpha or Primate family may be used. Animals of the family Rodentia include, for example, mouse, rat and hamster. Animals of the family Lagomorpha include, for example, rabbit. Animals of the Primate family include, for example, a monkey of Catarrhini (old world monkey) such as *Macaca fascicularis*, rhesus monkey, sacred baboon and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum may be examined by a standard method for an increase in the amount of desired antibodies.

Polyclonal antibodies against the peptides of the present invention may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum. Immunoglobulin G or M can be prepared from a fraction which recognizes only the peptide of the present invention using, for example, an affinity column coupled with the peptide of the present invention, and further purifying this fraction using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion may preferably be obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by the cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, the standard limiting dilution may be performed to screen and clone a hybridoma cell producing the desired antibody.

In addition to the above method, in which a non-human animal is immunized with an antigen for preparing hybridoma, human lymphocytes such as those infected by EB virus may be immunized with a peptide, peptide expressing cells or their lysates in vitro. Then, the immunized lymphocytes are fused with human-derived myeloma cells that are capable of indefinitely dividing, such as U266, to yield a hybridoma producing a desired human antibody that is able to bind to the peptide can be obtained (Unexamined Published Japanese Patent Application No. Sho 63-17688).

The obtained hybridomas are subsequently transplanted into the abdominal cavity of a mouse and the ascites are extracted. The obtained monoclonal antibodies can be purified by, for example, ammonium sulfate precipitation, a protein A or protein G column, DEAE ion exchange chromatography or an affinity column to which the peptide of the present invention is coupled. The antibody of the present invention can be used not only for purification and detection of the peptide of the present invention, but also as a candidate for agonists and antagonists of the peptide of the present invention.

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the peptides of the invention. For instance, the antibody fragment may be Fab, F(ab')$_2$, Fv or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector and expressed in an appropriate host cell (see, for example, Co et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, including the complementarity determining region (CDR) derived from nonhuman antibody, the frame work region (FR) and the constant region derived from human antibody. Such antibodies can be prepared according to known technology. Humanization can be performed by substituting rodent CDRs or CDR sequences for the corresponding sequences of a human antibody (see, e.g., Verhoeyen et al., Science 239: 1534-1536 (1988)). Accordingly, such humanized antibodies are chimeric antibodies, wherein substantially less than an intact human variable domain has been substituted by the corresponding sequence from a non-human species.

Fully human antibodies including human variable regions in addition to human framework and constant regions can also be used. Such antibodies can be produced using various techniques known in the art. For example, in vitro methods involve use of recombinant libraries of human antibody fragments displayed on bacteriophage (e.g., Hoogenboom & Winter, J. Mol. Biol. 227:381 (1991). Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; 5,661,016.

Antibodies obtained as above may be purified to homogeneity. For example, the separation and purification of the antibody can be performed according to the separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS and Sepharose F.F. (Pharmacia).

Exemplary chromatography, with the exception of affinity includes, for example, ion-exchange chromatography, hydrophobic chromatography, gel filtration, reverse phase chromatography, adsorption chromatography and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence may be used to measure the antigen binding activity of the antibody of the invention. In ELISA, the antibody of the present invention is immobilized on a plate, a peptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the peptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of the peptide of the invention, by exposing the antibody of the invention to a sample assumed to contain the peptide of the invention, and detecting or measuring the immune complex formed by the antibody and the peptide.

Because the method of detection or measurement of the peptide according to the invention can specifically detect or measure a peptide, the method can find use in a variety of experiments in which the peptide is used.

XII. VECTORS AND HOST CELLS

The present invention also provides a vector and host cell into which a nucleotide encoding the peptide of the present invention is introduced. A vector of the present invention can find use to keep a nucleotide, especially a DNA, of the present invention in host cell, to express the peptide of the present invention, or to administer the nucleotide of the present invention for gene therapy.

When $E.$ $coli$ is a host cell and the vector is amplified and produced in a large amount in $E.$ $coli$ (e.g., JM109, DH5 alpha, HB101 or XL1Blue), the vector should have "ori" to be amplified in $E.$ $coli$ and a marker gene for selecting transformed $E.$ $coli$ (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc., can be used. In addition, pGEM-T, pDIRECT and pT7 can also be used for subcloning and extracting cDNA as well as the vectors described above. When a vector is used to produce the protein of the present invention, an expression vector can find use. For example, an expression vector to be expressed in $E.$ $coli$ should have the above characteristics to be amplified in $E.$ $coli$. When $E.$ $coli$, such as JM109, DH5 alpha, HB101 or XL1 Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), T7 promoter or the like, that can efficiently express the desired gene in $E.$ $coli$. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for peptide secretion. An exemplary signal sequence that directs the peptide to be secreted to the periplasm of the $E.$ $coli$ is the pelB signal sequence (Lei et al., J Bacteriol 169: 4379 (1987)). Means for introducing of the vectors into the target host cells include, for example, the calcium chloride method, and the electroporation method.

In addition to $E.$ $coli$, for example, expression vectors derived from mammals (for example, pcDNA3 (Invitrogen) and pEGF-BOS (Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "$Pichia$ Expression Kit" (Invitrogen), pNV11, SP-Q01) and expression vectors derived from $Bacillus$ $subtilis$ (e.g., pPL608, pKTH50) can be used for producing the polypeptide of the present invention.

In order to express the vector in animal cells, such as CHO, COS or NIH3T3 cells, the vector should carry a promoter necessary for expression in such cells, for example, the SV40 promoter (Mulligan et al., Nature 277: 108 (1979)), the MMLV-LTR promoter, the EF1 alpha promoter (Mizushima et al., Nucleic Acids Res 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

The following examples are presented to illustrate the present invention and to assist one of ordinary skill in making and using the same. The examples are not intended in any way to otherwise limit the scope of the invention.

EXAMPLES

Materials and Methods

Cell Lines

T2 (HLA-A2), human B-lymphoblastoid cell line, and COST, African green monkey kidney cell line, were purchased from ATCC.

Candidate Selection of Peptides Derived from ECT2

9-mer and 10-mer peptides derived from ECT2 that bind to HLA-A*0201 molecule were predicted using binding prediction software "BIMAS" (www-bimas.citdcrtnih.gov/cgi-bin/molbio/hla_bindken_parker_comboform) (Parker et al. (J Immunol 1994, 152(1): 163-75), Kuzushima et al. (Blood 2001, 98(6): 1872-81)). These peptides were synthesized by Biosynthesis (Lewisville, Tex.) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethylsulfoxide at 20 mg/ml and stored at −80 degrees C.

In Vitro CTL Induction

Monocyte-derived dendritic cells (DCs) were used as antigen-presenting cells to induce cytotoxic T lymphocyte (CTL) responses against peptides presented on human leukocyte antigen (HLA). DCs were generated in vitro as described elsewhere (Nakahara S et al., Cancer Res 2003 Jul. 15, 63(14): 4112-8). Specifically, peripheral blood mononuclear cells (PBMCs) isolated from a normal volunteer (HLA-A*0201 positive) by Ficoll-Plaque (Pharmacia) solution were separated by adherence to a plastic tissue culture dish (Becton Dickinson) so as to enrich them as the monocyte fraction. The monocyte-enriched population was cultured in the presence of 1,000 U/ml of granulocyte-macrophage colony-stimulating factor (R&D System) and 1,000 U/ml of interleukin (IL)-4 (R&D System) in AIM-V Medium (Invitrogen) containing 2% heat-inactivated autologous serum (AS). After 7 days of culture, the cytokine-induced DCs were pulsed with 20 micro-g/ml of each of the synthesized peptides in the presence of 3 micro-g/ml of beta 2-microglobulin for 3 hrs at 37 degrees C. in AIM-V Medium. The generated cells appeared to express DC-associated molecules, such as CD80, CD83, CD86 and HLA class II, on their cell surfaces (data not shown). These peptide-pulsed DCs were then inactivated by X-irradiation (20 Gy) and mixed at a 1:20 ratio with autologous CD8+ T cells, obtained by positive selection with CD8 Positive Isolation Kit (Dynal). These cultures were set up in 48-well plates (Corning); each well contained $1.5\times10^4$ peptide-pulsed DCs, $3\times10^5$ CD8+ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On days 7 and 14, the T cells were further stimulated with the autologous peptide-pulsed DCs. The DCs were prepared each time by the same way described above. CTLs were tested against peptide-pulsed T2 cells after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

CTL Expansion Procedure

CTLs were expanded in culture using the method similar to the one described by Riddell et al. (Walter E A et al., N Engl J Med 1995 Oct. 19, 333(16): 1038-44; Riddell S R et al., Nat Med 1996 February, 2(2): 216-23). A total of $5\times10^4$ CTLs were suspended in 25 ml of AIM-V/5% AS medium with 2 kinds of human B-lymphoblastoid cell lines, inactivated by Mitomycin C, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 IU/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Establishment of CTL Clones

The dilutions were made to have 0.3, 1, and 3 CTLs/well in 96 round-bottomed micro titer plate (Nalge Nunc International). CTLs were cultured with $1\times10^4$ cells/well of 2 kinds of human B-lymphoblastoid cell lines, 30 ng/ml of anti-CD3 antibody, and 125 U/ml of IL-2 in a total of 150 micro-l/well of AIM-V Medium containing 5% AS. 50 micro-l/well of IL-2 were added to the medium 10 days later so to reach a final concentration of 125 U/ml IL-2. CTL activity was tested on the 14th day, and CTL clones were expanded using the same method as described above (Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Specific CTL Activity

To examine specific CTL activity, interferon (IFN)-gamma enzyme-linked immunospot (ELISPOT) assay and IFN-gamma enzyme-linked immunosorbent assay (ELISA) were performed. Specifically, peptide-pulsed T2 ($1\times10^4$/well) was prepared as stimulator cells. Cultured cells in 48 wells were used as responder cells. IFN-gamma ELISPOT assay and IFN-gamma ELISA assay were performed under manufacture procedure.

Establishment of the Cells Forcibly Expressing Either or Both of the Target Gene and HLA-A02

The cDNA encoding an open reading frame of target genes or HLA-A*0201 was amplified by PCR. The PCR-amplified product was cloned into a vector. The plasmids were transfected into COS7, which is the target genes and HLA-A*0201-null cell line, using lipofectamine 2000 (Invitrogen) according to the manufacturer's recommended procedures. After 2 days from transfection, the transfected cells were harvested with versene (Invitrogen) and used as the target cells ($5\times10^4$ cells/well) for CTL activity assay.

Results

Enhanced ECT2 Expression in Cancers

The global gene expression profile data obtained from various cancers using cDNA-microarray revealed that ECT2 (GenBank Accession No. AY376439; e.g., SEQ ID No: 41) expression was elevated. ECT2 expression was validly elevated in 17 out of 19 bladder cancer, 5 out of 12 breast cancer, 14 out of 14 cervical cancer, 13 out of 13 cholangiocellular carcinoma, 5 out of 5 CML, 7 out of 8 colorectal cancer, 12 out of 16 esophageal cancer, 6 out of 16 NSCLC, 8 out of 10 lymphoma, 1 out of 1 pancreatic cancer, 10 out of 13 prostate cancer, 3 out of 6 renal carcinoma and 12 out of 13 SCLC cancer as compared with corresponding normal tissue (Table 1).

TABLE 1

Ratio of cases observed up-regulation of ECT2 in cancerous tissue as compared with normal corresponding tissue.

| | |
|---|---|
| Bladder cancer | 17/19 |
| Breast cancer | 5/12 |
| Cervical cancer | 14/14 |
| Cholangiocellular carcinoma | 13/13 |
| CML | 5/5 |
| Colorectal cancer | 7/8 |
| Esophagus cancer | 12/16 |
| NSCLC | 6/16 |
| Lymphoma | 8/10 |
| Pancreatic cancer | 1/1 |
| Prostate cancer | 10/13 |
| Renal carcinoma | 3/6 |
| SCLC | 12/13 |

Prediction of HLA-A02 Binding Peptides Derived from ECT2

Tables 2a and 2b show the HLA-A02 binding 9mer and 10mer peptides of ECT2 in the order of high binding affinity. A total of 40 peptides with potential HLA-A02 binding ability were selected and examined to determine the epitope peptides.

TABLE 2a

HLA-A02 binding 9mer peptides derived from ECT2

| SEQ ID NO | Start Position | Amino Acid Sequence | Score |
|---|---|---|---|
| 1 | 34 | LLIGSTSYV | 650.311 |
| 2 | 619 | QIFDVVYEV | 333.677 |
| 3 | 664 | FLFNDCLEI | 177.566 |
| 4 | 662 | TLFLFNDCL | 147.174 |

TABLE 2a-continued

HLA-A02 binding 9mer peptides derived from ECT2

| SEQ ID NO | Start Position | Amino Acid Sequence | Score |
|---|---|---|---|
| 5 | 634 | LLSSHRSLV | 118.238 |
| 6 | 145 | MMNLVLCFT | 115.74 |
| 7 | 561 | LLIRPVQRL | 83.527 |
| 8 | 98 | VVTDFQDSV | 78.982 |
| 9 | 575 | LLNDLKKHT | 51.94 |
| 10 | 240 | FQDCILSFL | 50.414 |
| 11 | 292 | FEPSKKLYV | 34.216 |
| 12 | 823 | ALMTSHGSV | 33.455 |
| 13 | 220 | NEQDFYAAV | 31.606 |
| 14 | 755 | MLCRHVANT | 29.137 |
| 15 | 357 | AQLSRETDV | 26.092 |
| 16 | 438 | NILATIIQL | 24.997 |
| 17 | 874 | TLSRSTTHL | 21.362 |
| 18 | 568 | RLPSVALLL | 21.362 |
| 19 | 166 | TLVHHMGGV | 20.796 |
| 20 | 443 | IIQLFQVPL | 18.975 |

Start position indicates the number of amino acid residue from the N-terminus of ECT2 Binding score is derived from "BIMAS"

TABLE 2b

HLA-A02 binding 10mer peptides derived from ECT2

| SEQ ID NO | Start Position | Amino Acid Sequence | Score |
|---|---|---|---|
| 21 | 33 | NLLIgSTSYV | 1415.383 |
| 22 | 633 | NLLSsHRSLV | 257.342 |
| 23 | 144 | SMMNlVLCFT | 251.905 |
| 24 | 701 | LMPLsQIKKV | 196.407 |
| 25 | 754 | KMLCrHVANT | 160.303 |
| 26 | 557 | SLVElLIRPV | 131.175 |
| 27 | 191 | TQGEkFRVAV | 109.867 |
| 28 | 774 | YTADpESFEV | 105.669 |
| 29 | 428 | ELYQtESNYV | 91.809 |
| 30 | 618 | KQIFdVVYEV | 56.767 |
| 31 | 97 | FVVTdFQDSV | 52.126 |
| 32 | 20 | SIFDsKVTEI | 50.051 |
| 33 | 574 | LLLNdLKKHT | 46.873 |

TABLE 2b-continued

HLA-A02 binding 10mer peptides derived from ECT2

| SEQ ID NO | Start Position | Amino Acid Sequence | Score |
|---|---|---|---|
| 34 | 461 | ILAPeEIKTI | 40.792 |
| 35 | 664 | FLFNdCLEIA | 39.07 |
| 36 | 575 | LLNDlKKHTA | 34.627 |
| 37 | 430 | YQTEsNYVNI | 29.924 |
| 38 | 511 | DLVKtYPPFV | 28.69 |
| 39 | 471 | FGSIpDIFDV | 27.86 |
| 40 | 87 | GLDSpEFENV | 25.901 |

Start position indicates the number of amino acid residue from the N-terminus of ECT2 Binding score is derived from "BIMAS"

CTL Induction with the Predicted Peptides from ECT2 Restricted with HLA-A*0201

CTLs for those peptides derived from ECT2 were generated according to the protocols as described in "Materials and Methods". Peptide specific CTL activity was determined by IFN-gamma ELISPOT assay (FIGS. 1a-c). Well number #6 stimulated with ECT2-A02-9-34 (SEQ ID NO: 1) (a), well #5 stimulated with ECT2-A02-9-664 (SEQ ID NO: 3) (b) and well #1 stimulated with ECT2-A02-10-33 (SEQ ID NO: 21) (c) demonstrated potent IFN-gamma production as compared to the control wells. As a result, it indicated that ECT2-A02-9-34 (SEQ ID NO: 1) (a), ECT2-A02-9-664 (SEQ ID NO: 3) (b) and ECT2-A02-10-33 (SEQ ID NO: 21) (c) derived from ECT2 was screened as the peptides that could induce potent CTLs.

Establishment of CTL Lines and Clones Against ECT2 Derived Peptides

Figure 2:
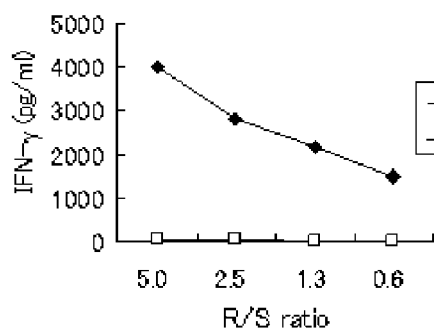
FIG. 2 is composed of a series of line graphs, (a) to (c), depicting the results of an IFN-gamma ELISA assay demonstrating the IFN-gamma production of CTL lines stimulated with (a) ECT2-A02-9-34 (SEQ ID NO: 1), (b) ECT2-A02-9-664 (SEQ ID NO: 3) and (c) ECT2-A02-10-33 (SEQ ID NO: 21). The results demonstrate that CTL lines established by stimulation with each peptide show potent IFN-gamma production as compared with the control. In the figures, "+" indicates the IFN-gamma production against target cells pulsed with the appropriate peptide, and "−" indicates the IFN-gamma production against target cells not pulsed with any peptides.
Figure 2:
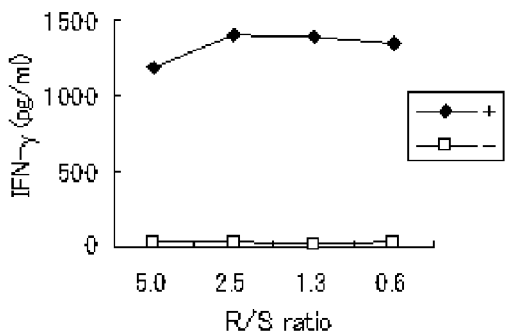
Figure 2:
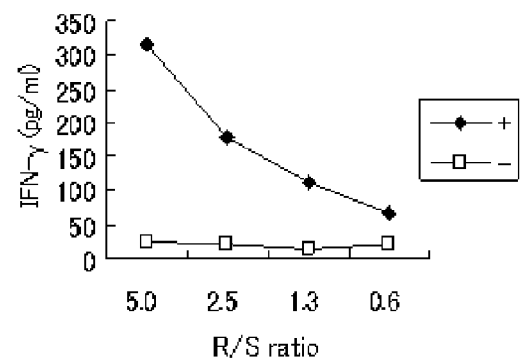
Figure 3:
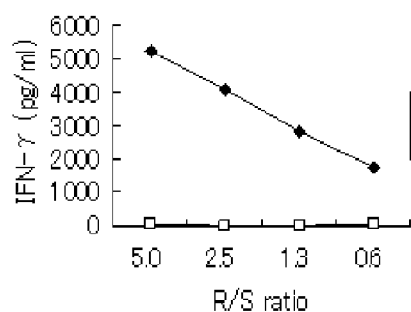
FIG. 3 depicts a pair of line graphs, (a) and (b), depicting the IFN-gamma production of CTL clones established by limiting dilution from the CTL lines stimulated with (a) ECT2-A02-9-34 (SEQ ID NO: 1) and (b) ECT2-A02-9-664 (SEQ ID NO: 3). The results demonstrate that CTL clones established by stimulation with each peptide showed potent IFN-gamma production as compared with the control. In the figure, "+" indicates the IFN-gamma production against target cells pulsed with the appropriate peptide and "−" indicates the IFN-gamma production against target cells not pulsed with any peptides.
Figure 3:
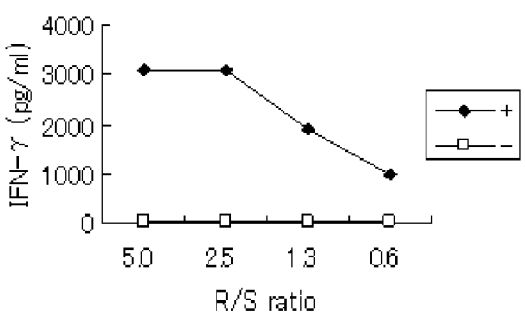

The cells that showed peptide specific CTL activity detected by IFN-gamma ELISPOT assay in the well number #6 stimulated with ECT2-A02-9-34 (SEQ ID NO: 1) (a), #5 stimulated with ECT2-A02-9-664 (SEQ ID NO: 3) (b) and #1 stimulated with ECT2-A02-10-33 (SEQ ID NO: 21) (c) were expanded and CTL lines were established by the limiting dilution process described above in the "Materials and Methods" section. CTL activity of these CTL lines was determined by IFN-gamma ELISA assay (FIGS. 2a-c). The CTL lines demonstrated potent IFN-gamma production against the target cells pulsed with the corresponding peptide as compared to target cells without peptide pulse. Furthermore, CTL clones was established by limiting dilution from CTL lines as described in "Materials and Methods", and IFN-gamma production from CTL clones against target cells pulsed peptide was determined by IFN-gamma ELISA assay. Potent IFN-gamma productions were determined from CTL clones stimulated with ECT2-A02-9-34 (SEQ ID NO: 1) (a) and ECT2-A02-9-664 (SEQ ID NO: 3) (b) in FIG. 3.

Specific CTL Activity Against Target Cells Exogenously Expressing ECT2 and HLA-A*0201

Figure 4:
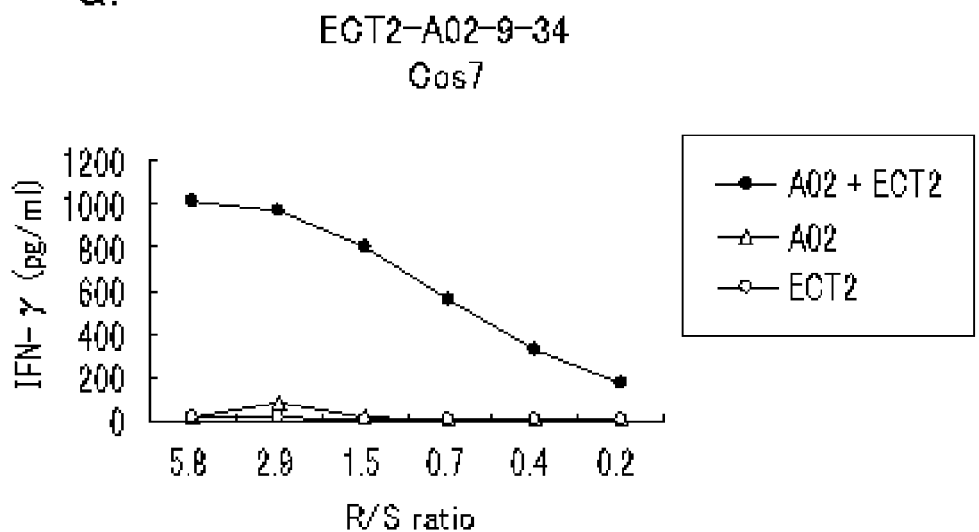
FIG. 4 depicts a pair of line graphs, (a) and (b), depicting specific CTL activity against target cells that exogenously express ECT2 and HLA-A*0201. COS7 cells transfected with HLA-A*0201 or the full length of ECT2 gene were prepared as control. The CTL clone established with ECT2-A02-9-34 (SEQ ID NO: 1) (a) and the CTL line established with ECT2-A02-10-33 (SEQ ID NO: 21) (b) showed specific CTL activity against COS7 cells transfected with both ECT2 and HLA-A*0201 (black circle). On the other hand, no significant specific CTL activity was detected against target cells expressing either HLA-A*0201 (triangle) or ECT2 (white circle).
Figure 4:
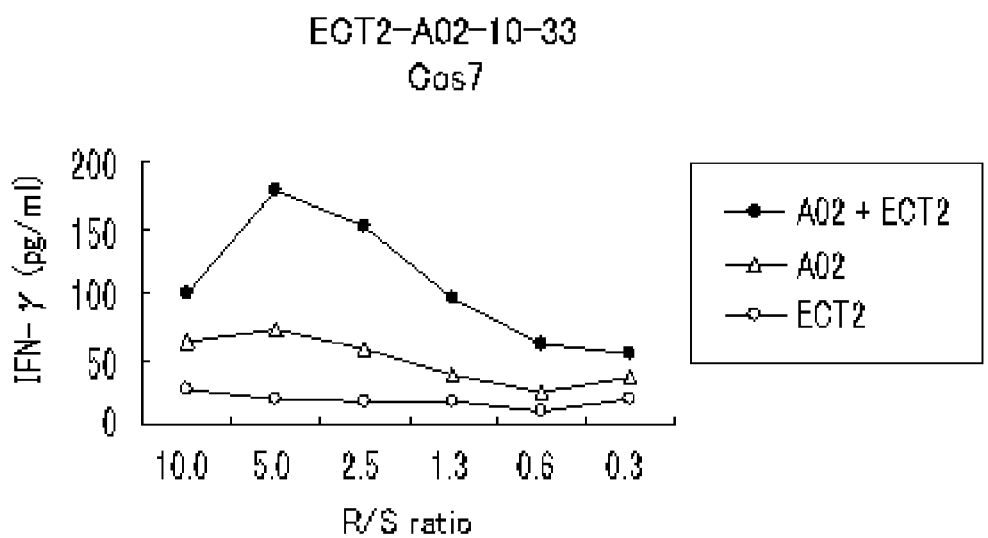

The established CTL lines and clones raised against these peptides was examined for the ability to recognize target cells that exogenously express ECT2 and HLA-A*0201 molecule. Specific CTL activity against COS7 cells which transfected with both the full length of ECT2 and HLA-A*0201 molecule gene (a specific model for the target cells that exogenously express ECT2 and HLA-A*0201 gene) was tested by using CTL lines and clones raised by corresponding peptide as the effector cells. COS7 cells transfected with either full length of ECT2 or HLA-A*0201 were prepared as the controls. In FIG. 4, the CTL clone stimulated with ECT2-A02-9-34 (SEQ ID NO: 1) (a) and the CTL line stimulated with ECT2-A02-10-33 (SEQ ID NO: 21) (b) showed potent CTL activity against COS7 cells expressing both ECT2 and HLA-A*0201. On the other hand, no significant specific CTL activity was detected against the controls. Thus, these data clearly demonstrated that ECT2-A02-9-34 (SEQ ID NO: 1) (a), ECT2-A02-10-33 (SEQ ID NO: 21) (b) were naturally expressed on the target cells with HLA-A*0201 molecule and were recognized by the CTLs. These results indicated that ECT2-A02-9-34 (SEQ ID NO: 1) (a) and ECT2-A02-10-33 (SEQ ID NO: 21) (b) derived from ECT2 may be suitable as a cancer vaccine for the treatment of patients with ECT2 expressing tumors.

Homology Analysis of Antigen Peptides

The CTLs stimulated with ECT2-A02-9-34 (SEQ ID NO: 1), ECT2-A02-9-664 (SEQ ID NO: 3) and ECT2-A02-10-33 (SEQ ID NO: 21) showed significant and specific CTL activity. This result may be due to the fact that the sequence of ECT2-A02-9-34 (SEQ ID NO: 1), ECT2-A02-9-664 (SEQ ID NO: 3) and ECT2-A02-10-33 (SEQ ID NO: 21) are homologous to peptide derived from other molecules that are known to sensitize the human immune system. To exclude this possibility, homology analyses were performed for these peptide sequences using as queries the BLAST algorithm (www.ncbi.nlm.nih.gov/blast/blast.cgi) which revealed no sequence with significant homology. The results of homology analyses indicate that the sequence of ECT2-A02-9-34 (SEQ ID NO: 1), ECT2-A02-9-664 (SEQ ID NO: 3) and ECT2-A02-10-33 (SEQ ID NO: 21) are unique and thus, there is little possibility, to our best knowledge, that these molecules raise unintended immunologic response to some unrelated molecule.

In conclusion, novel HLA-A2 epitope peptides derived from ECT2 were identified. Furthermore, it the results herein demonstrate that epitope peptides of ECT2 may be suitable for use in cancer immunotherapy.

INDUSTRIAL APPLICABILITY

The present invention provides new TAAs, particularly those derived from ECT2 that may induce potent and specific anti-tumor immune responses and have applicability to a wide variety of cancer types. Such TAAs can find use as peptide vaccines against diseases associated with ECT2, e.g., cancer, more particularly, bladder cancer, breast cancer, cervical cancer, cholangiocellular carcinoma, CML, colorectal cancer, esophageal cancer, NSCLC, lymphoma, pancreatic cancer, prostate cancer, renal carcinoma and SCLC.

While the present invention is herein described in detail and with reference to specific embodiments thereof, it is to be understood that the foregoing description is exemplary and explanatory in nature and is intended to illustrate the present invention and its preferred embodiments. Through routine experimentation, one skilled in the art will readily recognize that various changes and modifications can be made therein without departing from the spirit and scope of the present invention, the metes and bounds of which are defined by the appended claims.

The invention claimed is:

1. An isolated peptide of less than 15 amino acids having cytotoxic T lymphocyte (CTL) inducibility selected from the group consisting of:
   (a) an isolated peptide comprising an amino acid sequence selected from the group consisting of SEQ ID NOs: 1, 3 and 21, and
   (b) an isolated peptide having an amino acid sequence selected from the group consisting of SEQ ID NOs: 1, 3 and 21, in which 1 or 2 amino acid(s) are substituted or added.

2. The isolated peptide of claim 1, wherein the peptide has one or both of the following characteristics:
   (a) the second amino acid from the N-terminus of the amino acid sequence of SEQ ID NO: 1, 3 or 21 is substituted with methionine; and
   (b) the C-terminal amino acid of the amino acid sequence of SEQ ID NO: 1, 3 or 21 is substituted with an amino acid selected from the group consisting of valine and leucine.

3. The isolated peptide of claim 1, wherein said peptide is nonapeptide or decapeptide.

4. A composition for inducing CTL, wherein the composition comprises one or more peptide(s) of claim 1.

5. A pharmaceutical composition for the treatment of cancer over expressing ECT2, wherein the composition comprises one or more peptide(s) of claim 1.

6. The pharmaceutical composition of claim 5, wherein said pharmaceutical composition is formulated for the administration to a subject whose HLA antigen is HLA-A2.

7. A method for inducing an antigen-presenting cell (APC) with CTL inducibility comprising contacting an APC with the peptide of claim 1 in vitro, .ex vivo or in vivo.

8. A method for inducing CTL by a method that comprises a step selected from the group consisting of:
   (a) co-culturing CD8 positive T cells with APCs that present on the surface a complex of an HLA antigen and the peptide of claim 1; and
   (b) co-culturing CD8 positive T cells with exosomes that present on the surface a complex of an HLA antigen and the peptide of claim 1.

9. A method of inducing an immune response against cancer over expressing ECT2 in a subject in need thereof, said method comprising the step of administering to the subject a composition comprising the peptide of claim 1, an immunologically active fragment thereof.

10. A kit comprising any of the peptides of claim 1.

11. The isolated peptide of claim 1, wherein the peptide consists of the amino acid sequence selected from the group consisting of SEQ ID NOs: 1, 3 and 21.

12. The composition of claim 4, wherein the composition comprises a pharmaceutically acceptable carrier, wherein the pharmaceutically acceptable carrier is sterilized water, physiological saline or phosphate buffer.

13. The pharmaceutical composition of claim 5, wherein the pharmaceutical composition comprises a pharmaceutically acceptable carrier, wherein the pharmaceutically acceptable carrier is sterilized water, physiological saline or phosphate buffer.

14. The pharmaceutical composition of claim 5, wherein the pharmaceutical composition comprises Incomplete Freund's adjuvant as an adjuvant.

15. The method of claim 9, wherein a dose of the peptide is 0.1 mg to 10 mg.

16. The method of claim 9, wherein the method comprises a step of administering the composition with an adjuvant.

* * * * *